US012734037B2

(12) United States Patent
Sharp et al.

(10) Patent No.: US 12,734,037 B2
(45) Date of Patent: Sep. 15, 2026

(54) POROUS IMPLANT STRUCTURES

(71) Applicant: Smith & Nephew, Inc., Memphis, TN (US)

(72) Inventors: Jeffrey Sharp, Salt Lake City, UT (US); Shilesh Jani, Memphis, TN (US); Laura Gilmour, Alameda, CA (US); Ryan Landon, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 164 days.

(21) Appl. No.: 18/822,796

(22) Filed: Sep. 3, 2024

(65) Prior Publication Data

US 2024/0423802 A1 Dec. 26, 2024

Related U.S. Application Data

(60) Continuation of application No. 18/370,685, filed on Sep. 20, 2023, now Pat. No. 12,102,536, which is a (Continued)

(51) Int. Cl.
*A61F 2/28* (2006.01)
*A61F 2/30* (2006.01)
(Continued)

(52) U.S. Cl.
CPC ................ *A61F 2/28* (2013.01); *A61L 27/56* (2013.01); *B33Y 10/00* (2014.12); *B33Y 70/00* (2014.12);
(Continued)

(58) Field of Classification Search
None
See application file for complete search history.

(56) References Cited

U.S. PATENT DOCUMENTS 4,863,538 A 9/1989 Deckard
4,944,817 A 7/1990 Bourell et al.
(Continued)

FOREIGN PATENT DOCUMENTS

CA 2162561 C 8/2000
CA 2407073 A1 11/2001
(Continued)

OTHER PUBLICATIONS

First Office Action for Chinese Patent Application No. 201610703368.3, mailed May 13, 2019.
(Continued)

*Primary Examiner* — Anthony M Liang
(74) *Attorney, Agent, or Firm* — KDW Firm PLLC

(57) ABSTRACT

Porous biocompatible structures suitable for use as medical implants and methods for fabricating such structures are disclosed. The disclosed structures may be fabricated using rapid manufacturing techniques. The disclosed porous structures each have a plurality of struts and nodes where no more than two struts intersect one another to form a node. Further, the nodes can be straight, curved, and can include portions that are curved and/or straight. The struts and nodes can form cells that can be fused or sintered to at least one other cell to form a continuous reticulated structure for improved strength while providing the porosity needed for tissue and cell in-growth.

36 Claims, 33 Drawing Sheets

Related U.S. Application Data continuation of application No. 17/988,003, filed on Nov. 16, 2022, now Pat. No. 11,793,645, which is a continuation of application No. 17/158,397, filed on Jan. 26, 2021, now Pat. No. 11,529,235, which is a division of application No. 15/603,936, filed on May 24, 2017, now Pat. No. 10,945,847, which is a division of application No. 13/391,126, filed as application No. PCT/US2010/046032 on Aug. 19, 2010, now Pat. No. 9,668,863.

(60) Provisional application No. 61/235,269, filed on Aug. 19, 2009.

(51) Int. Cl.

| | |
|---|---|
| ***A61L 24/00*** | (2006.01) |
| ***A61L 27/56*** | (2006.01) |
| ***B33Y 10/00*** | (2015.01) |
| ***B33Y 70/00*** | (2020.01) |
| ***B33Y 70/10*** | (2020.01) |
| ***B33Y 80/00*** | (2015.01) |

(52) U.S. Cl.

CPC ............... *B33Y 70/10* (2020.01); *B33Y 80/00* (2014.12); *A61F 2002/3028* (2013.01); *A61F 2002/30593* (2013.01); *A61F 2002/30914* (2013.01); *A61F 2002/3092* (2013.01); *A61F 2002/30962* (2013.01); *A61F 2230/0063* (2013.01); *A61L 24/0036* (2013.01); *Y10T 29/49826* (2015.01)

(56) References Cited

U.S. PATENT DOCUMENTS

| | | | |
|---|---|---|---|
| 5,017,753 | A | 5/1991 | Deckard |
| 5,076,869 | A | 12/1991 | Bourell et al. |
| 5,490,962 | A | 2/1996 | Cima et al. |
| 5,518,680 | A | 5/1996 | Cima et al. |
| 5,622,542 | A | 4/1997 | Thomas et al. |
| 5,639,402 | A | 6/1997 | Barlow et al. |
| 5,786,562 | A | 7/1998 | Larson |
| 5,869,170 | A | 2/1999 | Cima et al. |
| 6,165,193 | A | 12/2000 | Greene, Jr. et al. |
| 6,176,874 | B1 | 1/2001 | Vacanti et al. |
| 6,183,515 | B1 | 2/2001 | Barlow et al. |
| 6,283,997 | B1 | 9/2001 | Garg et al. |
| 6,322,728 | B1 | 11/2001 | Brodkin et al. |
| 6,333,029 | B1 | 12/2001 | Vyakamam et al. |
| 6,412,232 | B1 | 7/2002 | Provitola |
| 6,454,811 | B1 | 9/2002 | Sherwood et al. |
| 6,530,958 | B1 | 3/2003 | Cima et al. |
| 6,540,045 | B1 | 4/2003 | Widmer et al. |
| 6,540,784 | B2 | 4/2003 | Barlow et al. |
| 6,660,208 | B2 | 12/2003 | Hanna |
| 6,827,178 | B2 | 12/2004 | Widmer et al. |
| 6,849,223 | B2 | 2/2005 | Dean et al. |
| 6,863,151 | B2 | 3/2005 | Widmer et al. |
| 6,932,610 | B2 | 8/2005 | Ono et al. |
| 6,994,549 | B2 | 2/2006 | Brodkin et al. |
| 6,996,245 | B2 | 2/2006 | Hanna |
| 7,014,010 | B2 | 3/2006 | Widmer |
| 7,431,874 | B2 | 10/2008 | Muratoglu et al. |
| 7,452,500 | B2 | 11/2008 | Uckelmann |
| 7,454,262 | B2 | 11/2008 | Larsson |
| 7,483,558 | B2 | 1/2009 | Greene, Jr. et al. |
| 7,497,876 | B2 | 3/2009 | Tuke et al. |
| 7,498,365 | B2 | 3/2009 | Muratoglu et al. |
| 7,509,240 | B2 | 3/2009 | Das et al. |
| 2002/0187458 | A1 | 12/2002 | Dolabdjian et al. |
| 2003/0069638 | A1 | 4/2003 | Barlow et al. |
| 2003/0114936 | A1 | 6/2003 | Sherwood et al. |
| 2003/0220696 | A1 | 11/2003 | Levine et al. |
| 2004/0026807 | A1 | 2/2004 | Andersson et al. |
| 2004/0191106 | A1 | 9/2004 | O'Neill et al. |
| 2004/0197737 | A1 | 10/2004 | Uckelmann et al. |
| 2004/0201139 | A1 | 10/2004 | Widmer et al. |
| 2005/0008990 | A1 | 1/2005 | Ganz et al. |
| 2005/0023710 | A1 | 2/2005 | Brodkin et al. |
| 2005/0056350 | A1 | 3/2005 | Dolabdjian et al. |
| 2005/0112397 | A1 | 5/2005 | Rolfe et al. |
| 2006/0140813 | A1 | 6/2006 | Rabiei |
| 2006/0141089 | A1 | 6/2006 | Larsson et al. |
| 2006/0145381 | A1 | 7/2006 | Larsson |
| 2006/0147332 | A1 | 7/2006 | Jones et al. |
| 2006/0157454 | A1 | 7/2006 | Larsson |
| 2006/0157892 | A1 | 7/2006 | Larsson |
| 2006/0245987 | A1 | 11/2006 | Schmidt |
| 2007/0033805 | A1 | 2/2007 | Jonsson et al. |
| 2007/0065779 | A1 | 3/2007 | Mangano |
| 2007/0082321 | A1 | 4/2007 | Uckelmann et al. |
| 2007/0142914 | A1 | 6/2007 | Jones et al. |
| 2007/0175875 | A1 | 8/2007 | Uckelmann et al. |
| 2007/0203584 | A1 | 8/2007 | Bandyopadhyay et al. |
| 2007/0219638 | A1 | 9/2007 | Jones et al. |
| 2007/0264152 | A1 | 11/2007 | Zhao |
| 2008/0004709 | A1 | 1/2008 | O'Neill et al. |
| 2008/0050412 | A1 | 2/2008 | Jones et al. |
| 2008/0131479 | A1 | 6/2008 | Weber et al. |
| 2008/0153069 | A1 | 6/2008 | Holzner et al. |
| 2008/0200976 | A1 | 8/2008 | Asgari |
| 2008/0206710 | A1 | 8/2008 | Kruth et al. |
| 2008/0241788 | A1 | 10/2008 | Bauer et al. |
| 2008/0241798 | A1 | 10/2008 | Holzner et al. |
| 2009/0051082 | A1 | 2/2009 | Nakamura et al. |
| 2009/0068245 | A1 | 3/2009 | Noble et al. |
| 2009/0068616 | A1 | 3/2009 | Uckelmann |
| 2009/0072450 | A1 | 3/2009 | Wallgren et al. |
| 2009/0075237 | A1 | 3/2009 | Garcia-Aparicio |
| 2009/0112250 | A1 | 4/2009 | Greene, Jr. et al. |
| 2010/0010638 | A1 | 1/2010 | Jones et al. |
| 2010/0291401 | A1 | 11/2010 | Medina et al. |

FOREIGN PATENT DOCUMENTS

| | | | |
|---|---|---|---|
| CA | 2173318 | C | 1/2002 |
| CA | 2506810 | A1 | 7/2004 |
| CA | 2507695 | A1 | 7/2004 |
| CA | 2507696 | A1 | 7/2004 |
| CA | 2507698 | A1 | 7/2004 |
| CA | 2508107 | A1 | 7/2004 |
| CA | 2295896 | C | 5/2005 |
| CA | 2557049 | A1 | 9/2005 |
| CA | 2529884 | A1 | 6/2006 |
| CA | 2569773 | A1 | 6/2007 |
| CA | 2625761 | A1 | 9/2008 |
| CA | 2222323 | C | 8/2009 |
| CA | 2572095 | C | 12/2009 |
| CA | 2448592 | C | 1/2011 |
| CN | 101292914 | A | 10/2008 |
| CN | 101292915 | A | 10/2008 |
| CN | 101301230 | A | 11/2008 |
| CN | 101310964 | A | 11/2008 |
| CN | 101410208 | A | 4/2009 |
| DE | 10315563 | A1 | 10/2004 |
| DE | 102004009127 | A1 | 9/2005 |
| DE | 102006061143 | A1 | 7/2008 |
| EP | 0724428 | A1 | 8/1996 |
| EP | 0714333 | B1 | 8/1999 |
| EP | 1245369 | A2 | 10/2002 |
| EP | 1296788 | B1 | 1/2005 |
| EP | 1418013 | B1 | 1/2005 |
| EP | 1583624 | A1 | 10/2005 |
| EP | 1583625 | A1 | 10/2005 |
| EP | 1583627 | A1 | 10/2005 |
| EP | 11583626 | A1 | 10/2005 |
| EP | 11583628 | A1 | 10/2005 |
| EP | 1596755 | A2 | 11/2005 |
| EP | 1683592 | A1 | 7/2006 |
| EP | 1683593 | A2 | 7/2006 |
| EP | 1764061 | A1 | 3/2007 |
| EP | 1568472 | B1 | 4/2007 |
| EP | 1776935 | A1 | 4/2007 |

(56) References Cited

FOREIGN PATENT DOCUMENTS

| | | | |
|---|---|---|---|
| EP | 1021997 81 | | 5/2007 |
| EP | 1464298 | B1 | 5/2007 |
| EP | 1800700 | A2 | 6/2007 |
| EP | 1803513 | A2 | 7/2007 |
| EP | 1848365 | A1 | 10/2007 |
| EP | 11879711 | A1 | 1/2008 |
| EP | 11911468 | A2 | 4/2008 |
| EP | 1776936 | B1 | 5/2008 |
| EP | 1919402 | A1 | 5/2008 |
| EP | 1974688 | A1 | 10/2008 |
| EP | 1997453 | A1 | 12/2008 |
| EP | 1720676 | B1 | 1/2009 |
| EP | 2049289 | A1 | 4/2009 |
| EP | 2054537 | A1 | 5/2009 |
| EP | 1683593 | A3 | 6/2010 |
| GB | 2395927 | B | 8/2006 |
| GB | 2431354 | A | 4/2007 |
| IN | 00300DEL2007 | | 8/2007 |
| IN | 01033CHENP2005 | | 9/2007 |
| IN | 10565DELNP2008 | | 3/2009 |
| IT | 20051717 | | 3/2007 |
| IT | 20070092 | | 11/2008 |
| JP | 04364858 | A | 12/1992 |
| JP | 3038397 | B2 | 5/2000 |
| JP | 2003513879 | A | 4/2003 |
| JP | 2003525696 | A | 9/2003 |
| JP | 2004184606 | A | 7/2004 |
| JP | 2004532080 | A | 10/2004 |
| JP | 2008540100 | A | 11/2008 |
| KR | 20080014029 | A | 2/2008 |
| RU | 2218242 | C2 | 12/2003 |
| SE | 520709 | C2 | 8/2003 |
| SE | 520710 | C2 | 8/2003 |
| WO | 9511007 | A1 | 4/1995 |
| WO | 9640002 | A1 | 12/1996 |
| WO | 2001036013 | A2 | 5/2001 |
| WO | 2002066044 | A2 | 8/2002 |
| WO | 02085246 | A2 | 10/2002 |
| WO | 2002092882 | A1 | 11/2002 |
| WO | 03034314 | A1 | 4/2003 |
| WO | 2007101898 | A2 | 9/2007 |
| WO | 08147306 | A1 | 12/2008 |
| WO | 2008146141 | A2 | 12/2008 |
| WO | 09014718 | A1 | 1/2009 |

OTHER PUBLICATIONS

Search Report for Chinese Patent Application No. 201610703368.3, mailed May 13, 2019.

Decision of Rejection for Japanese Patent Application No. 2017-157431, mailed May 7, 2019.

Indian Office Action; Intellectual Property Office of India; Indian Patent Application No. 1464/DELNP/2012; Jan. 31, 2019; 10 pages.

Indian Office Action; Intellectual Property Office of India; Indian Patent Application No. 1464/DELNP/2012; Dec. 24, 2018; 6 pages.

Canadian Office Action; Canadian Intellectual Property Office; Canadian Patent Application No. 2,771,384; Nov. 22, 2018; 3 pages.

Canadian Office Action; Canadian Intellectual Property Office; Canadian Patent Application No. 2,771,317; Aug. 17, 2018; 4 pages.

Japanese Notice of Reasons for Rejection, Japanese Patent Office, Japanese Patent Application No. 2017-157431, May 7, 2018; 7 pages.

Communication pursuant to Article 94(3) for Application No. EP 18199395.7, dated Nov. 18, 2020, 6 pages.

European Patent Office, European Search Report, dated May 24, 2024, 6 pages.

Image from Trans Globe Lighting, archived on Aug. 4, 2008 by Google.com; Accessed on Nov. 12, 2013 Full web address is listed o the second page of document.

Trans Globe Lighting "Bird Cage 18" Pendant Brown, Accessed on Oct. 29, 2013 http://www.tglighting.com/transglobe/product-details.aspx/product/bird-cage-18--pendant-brown-pnd-820 *Zoomed Image with examiner's modifications included.

Heck, V.; "Valerie A. Heck: The inspiration of Jewelry Artist Goldsmith, & Entrepreneur", 2008, http://valerieaheck.blogspot.com/2008/07/jewelry-i-made-last-summer.html#.U2p-ScX7Lco.

"Jewelry Making: Jump Ring Usage", 2005 http://www.bloglander.com/jewelrymaking/articles/using_jump_rings/1/Page with date referencing above article and link to article is also attached. www.bloglander.com/jewelrymaking/2005/06/01/using_jump_rings_article/.

The Beadery, Greene Plastics Corporation, "Making Your Own Jewelry: Tools, Tips, & Techniques", 2005, p. 1-2. Accessed at http://www.thebeadery.com/tips/E-0504_Jewelry-Making.pdf.

Body Jewellery Shop, "Titanium", 2005, p. 1-3; Accessed on Jan. 14, 2015 at http://web.archive.org/web/20080715234108/http://www.bodyjewelleryshop.com/online_store/titanium_316.cfm.

English language translation of EP 1917877 A1, generated on Jan. 14, 2015 with Espacenet.com.

Wettergreen, M.A.; Bucklen, B.S.; Starly, B.; Yuksel, E.; Sun, W.; Liebschner, M.A.K.; Creation of a Unit Block Library of Architectures for the Use in Assembled Scaffold Engineering:, Computer Aided Design, 2005, vol. 37, p. 1141-1149.

International Search Report and Written Opinion issued for PCT/US2010/046032, dated Oct. 7, 2010, 7 pages.

Chinese Second Office Action; State Intellectual Property Office of People's Republic of China; Chinese Application No. 201080047154.6; Oct. 22, 2014; 23 pages.

Chinese Third Office Action; State Intellectual Property Office of People's Republic of China; Chinese Application No. 201080047154.6; Apr. 14, 2015; 20 pages.

Chinese Second Office Action; State Intellectual Property Office of People's Republic of China; Chinese Application No. 201080047155.0; Jan. 19, 2015; 26 pages.

Chinese Third Office Action; State Intellectual Property Office of People's Republic of China; Chinese Application No. 201080047155.0; Aug. 14, 2015; 8 pages.

Australian Examination Report No. 1; Australian Patent Office; Australian Patent Application No. 2010284207; Jan. 9, 2015; 3 pages.

Japanese First Office Action; Japanese Patent Office; Japanese Application No. 2012-525699; mailed May 26, 2014; 4 pages.

Chinese First Office Action; State Intellectual Property Office of People's Republic of China; Chinese Application No. 201080047154.6; Mar. 5, 2014; 22 pages.

Chinese First Office Action; State Intellectual Property Office of People's Republic of China; Chinese Application No. 201080047155.0; Mar. 28, 2014; 23 pages.

European First Office Action; European Patent Office; European Application No. 10810598.2; May 22, 2014; 5 pages.

European First Office Action; European Patent Office; European Application No. 10810605.5; May 22, 2014; 6 pages.

Building Structure; Edited by Si Chuan, Water Power College; Apr. 30, 1982; pp. 178-180.

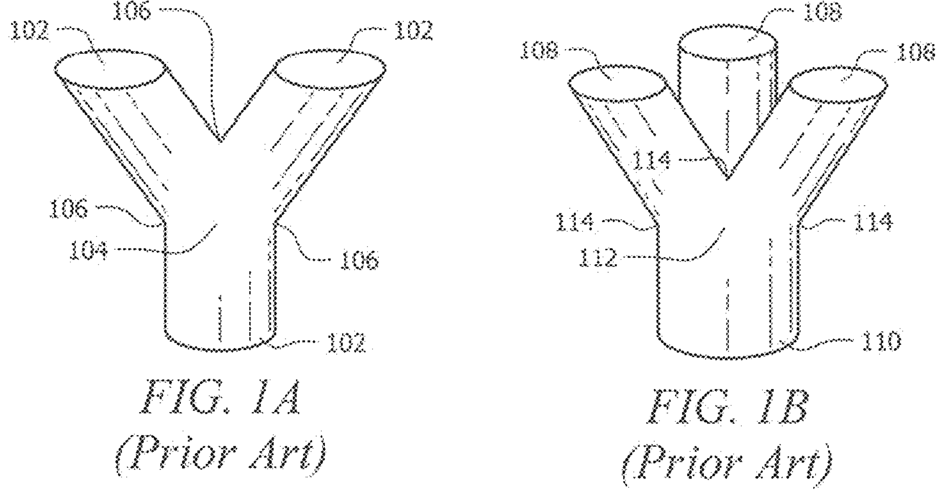
FIG. 1A
(Prior Art)
FIG. 1B
(Prior Art)
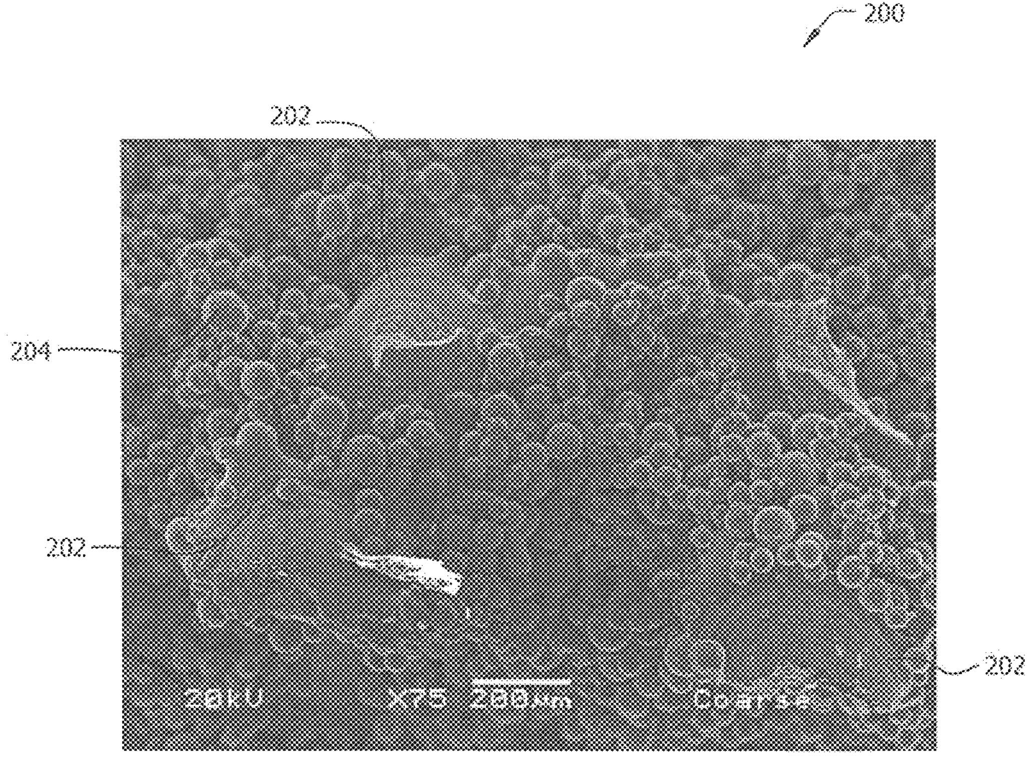
FIG. 2

1002

1104
1102

1002

1102
1104

1002

1102
1104

1002

1102
1104

1002

1102
1104

1002

1102
1104

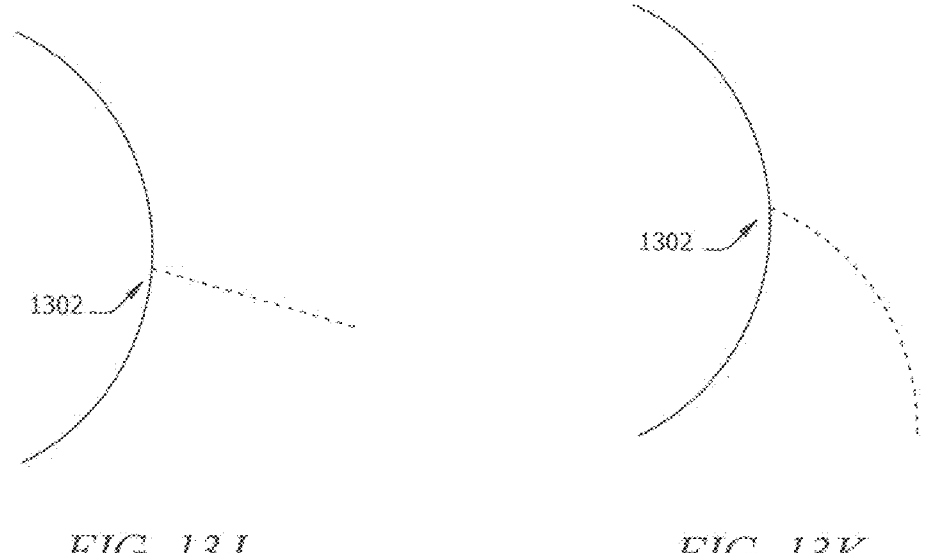
FIG. 13J
FIG. 13K
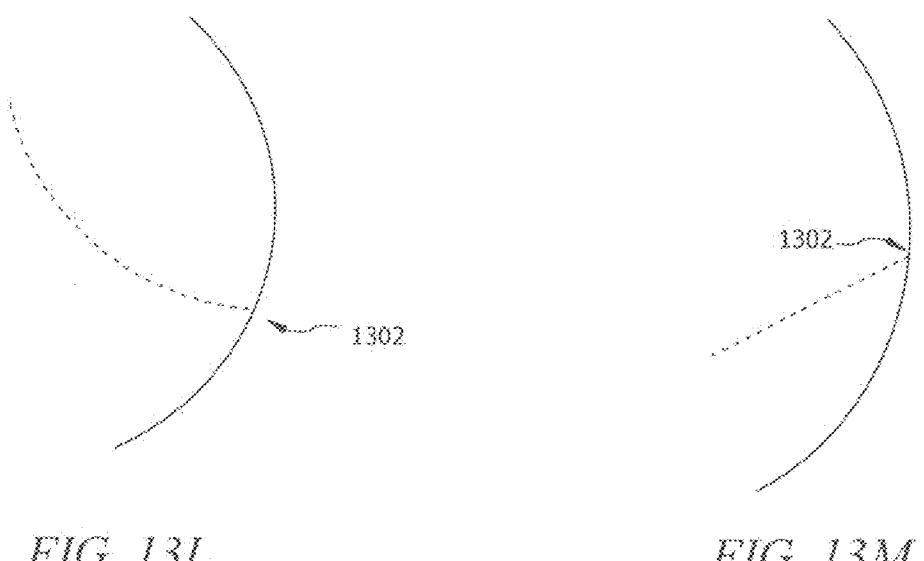
FIG. 13L
FIG. 13M

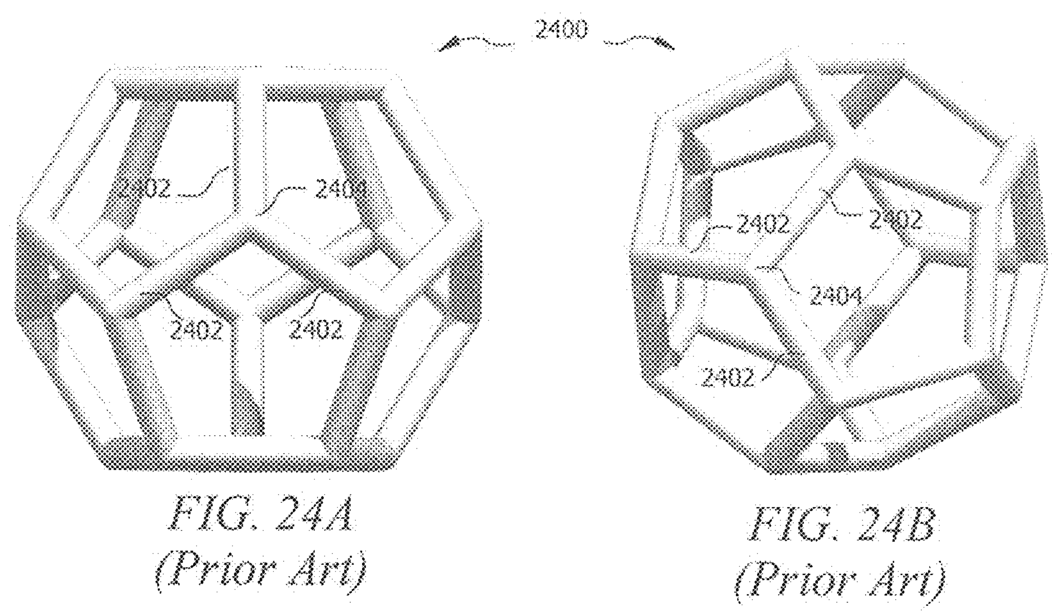
FIG. 24A
(Prior Art)
FIG. 24B
(Prior Art)
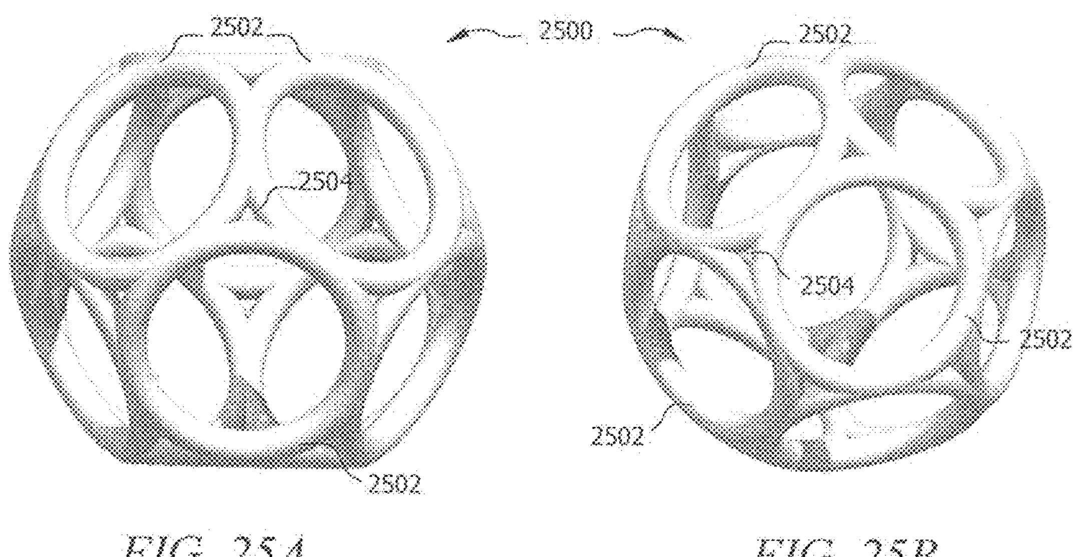
FIG. 25A
FIG. 25B

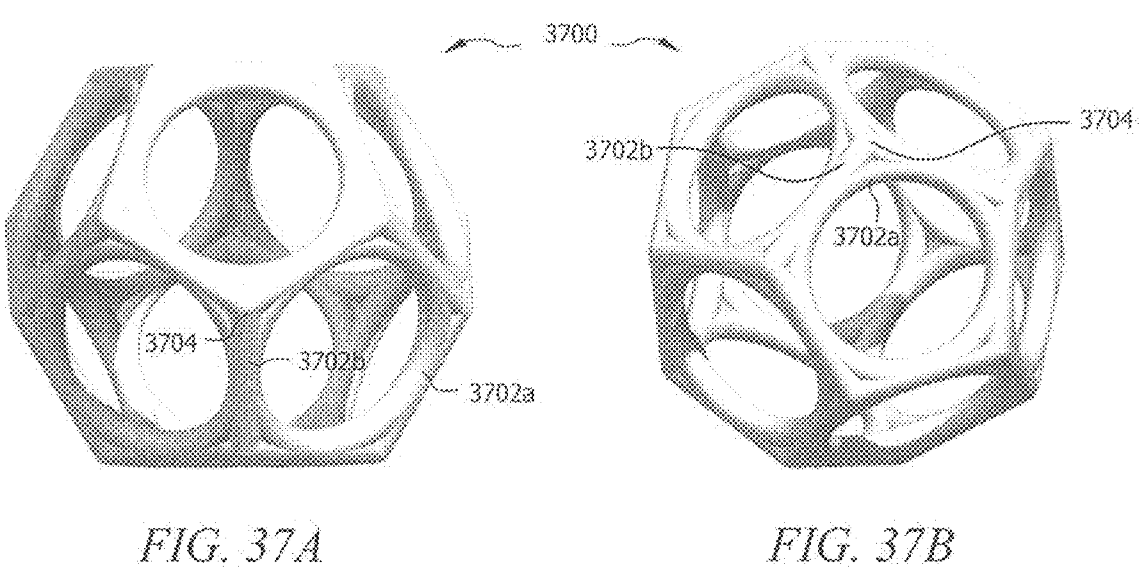
FIG. 37A
FIG. 37B
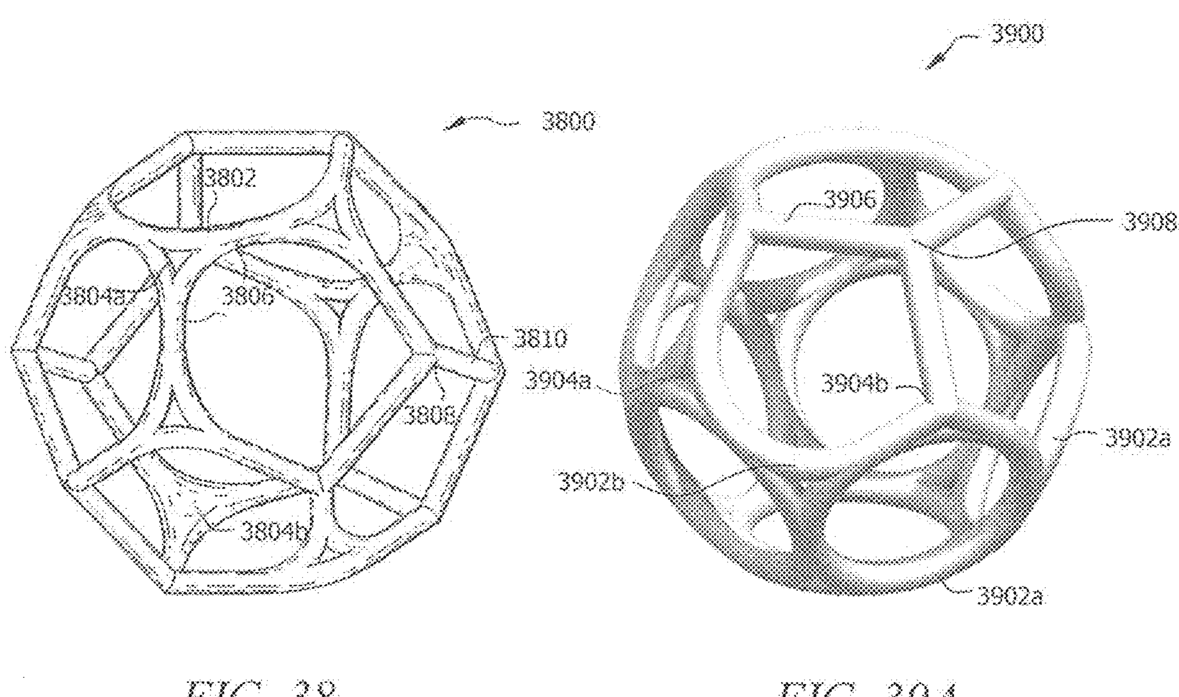
FIG. 38
FIG. 39A

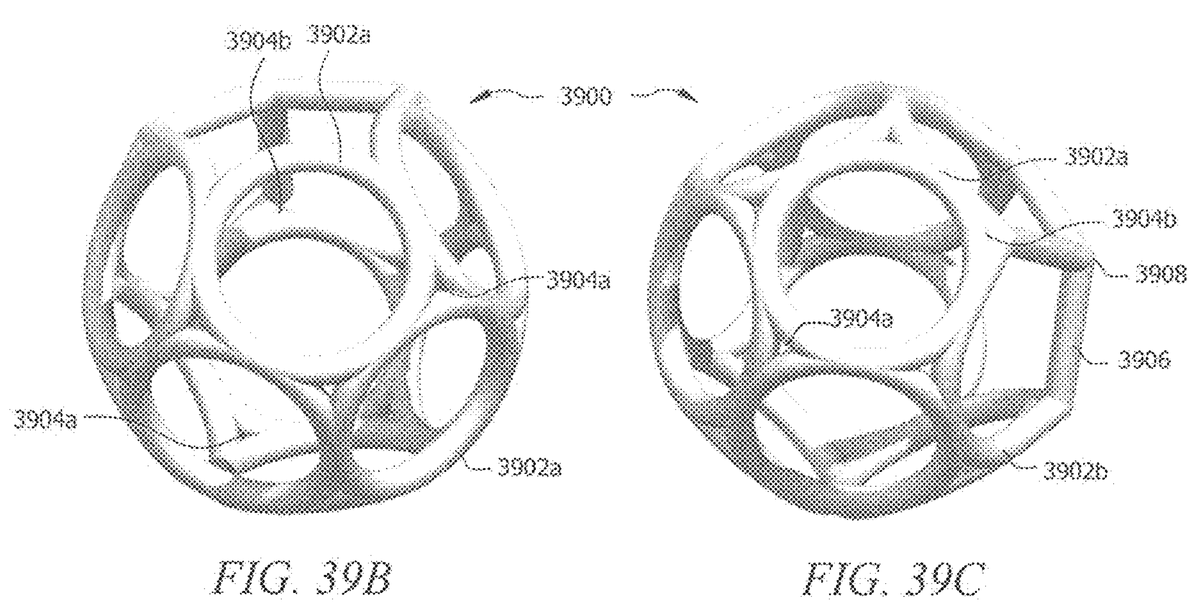
FIG. 39B
FIG. 39C
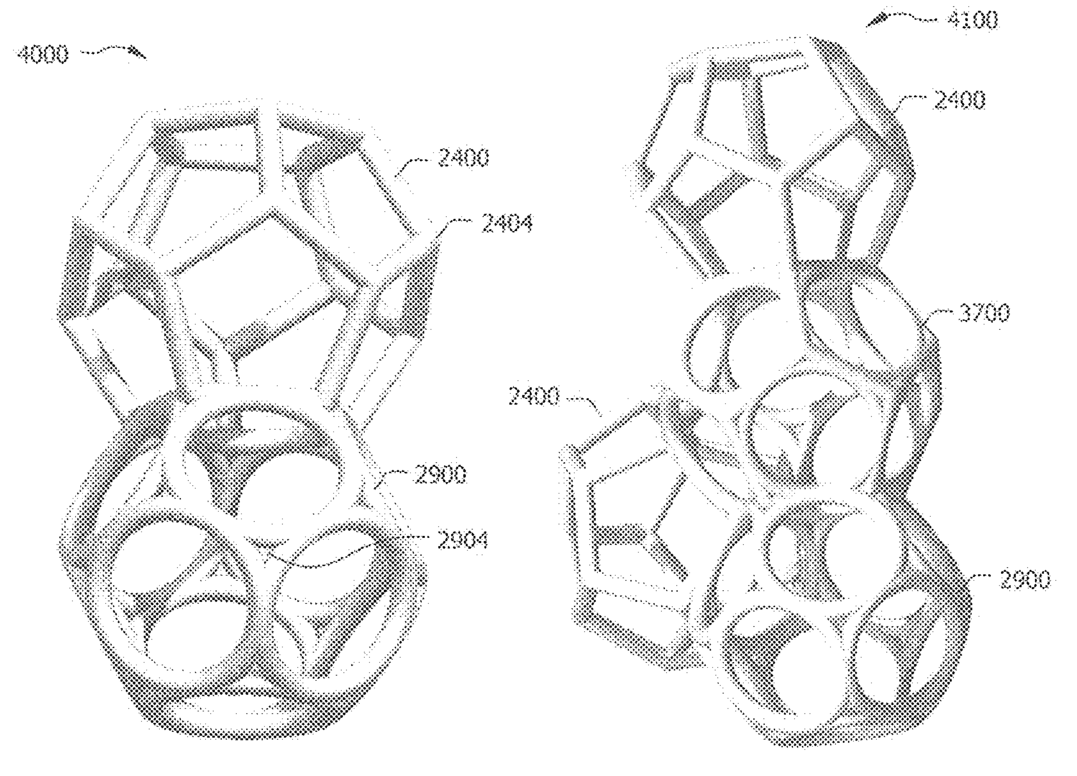
FIG. 40
FIG. 41A

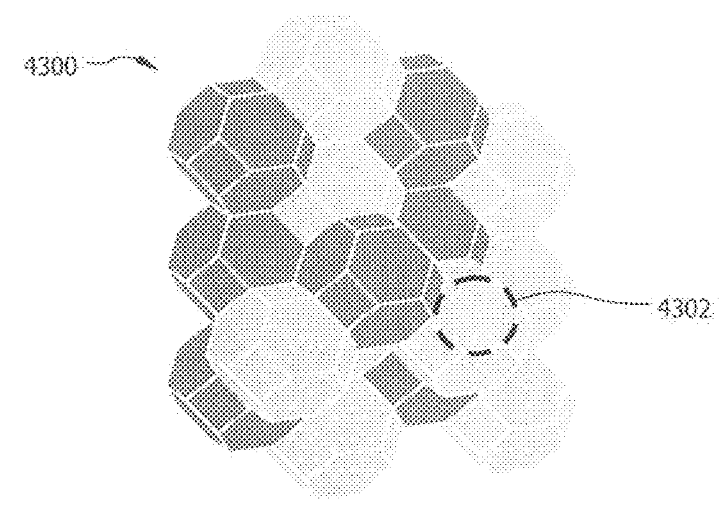
FIG. 43
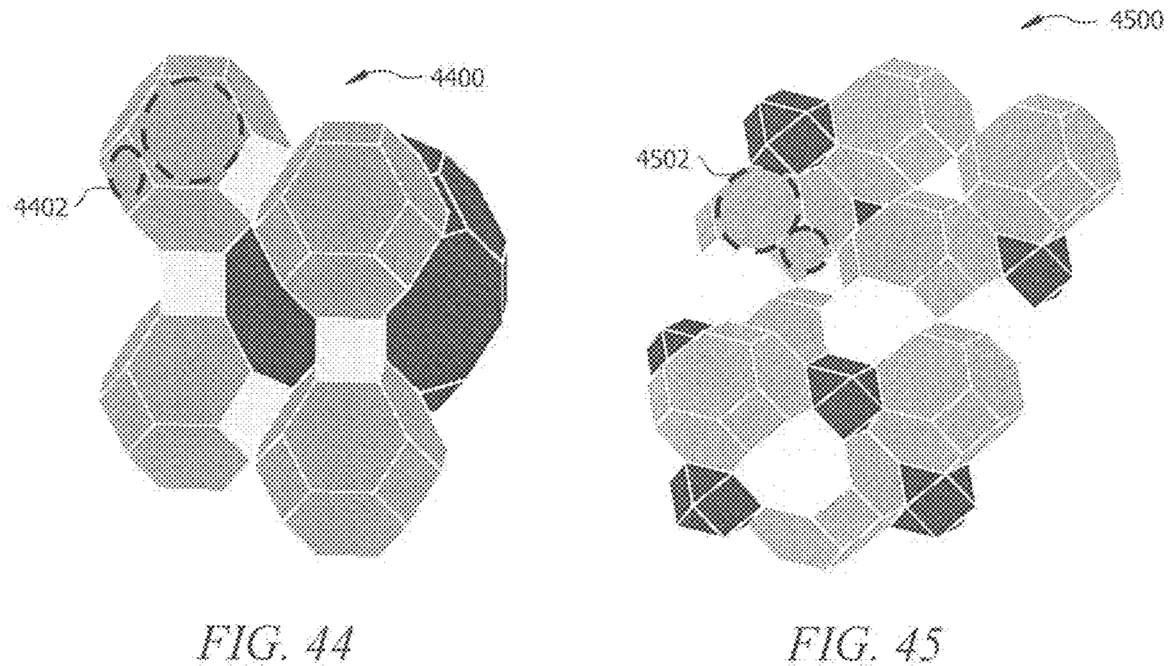
FIG. 44
FIG. 45

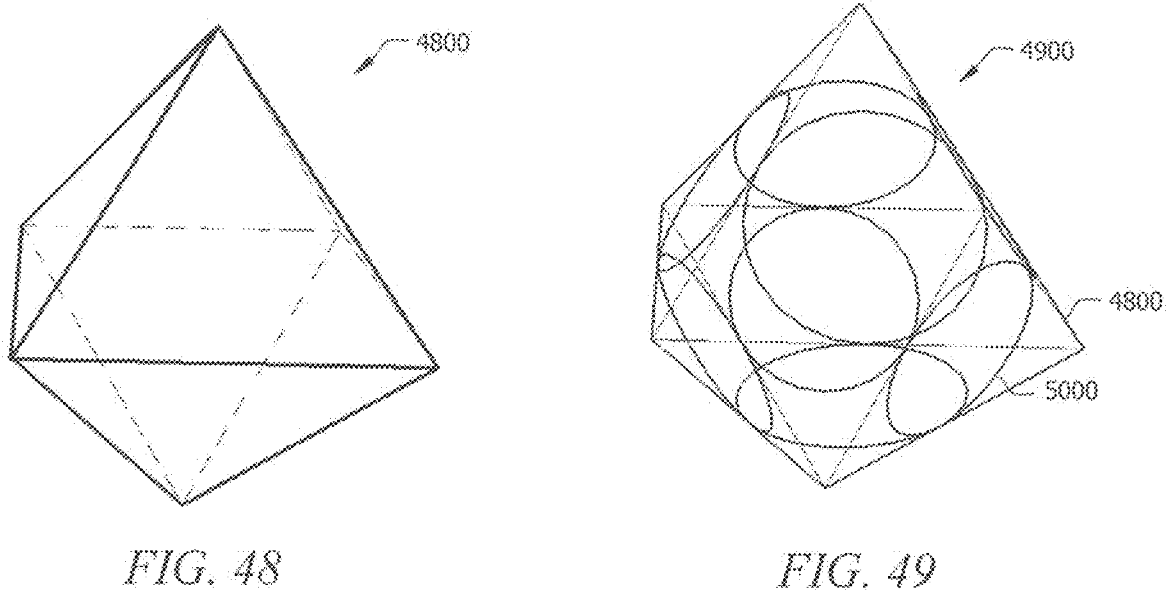
FIG. 48
FIG. 49
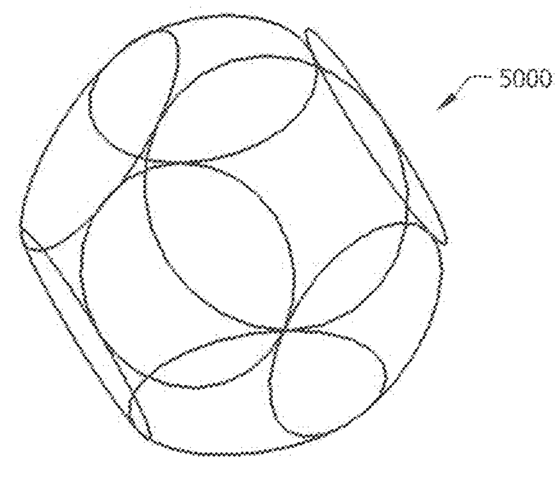
FIG. 50

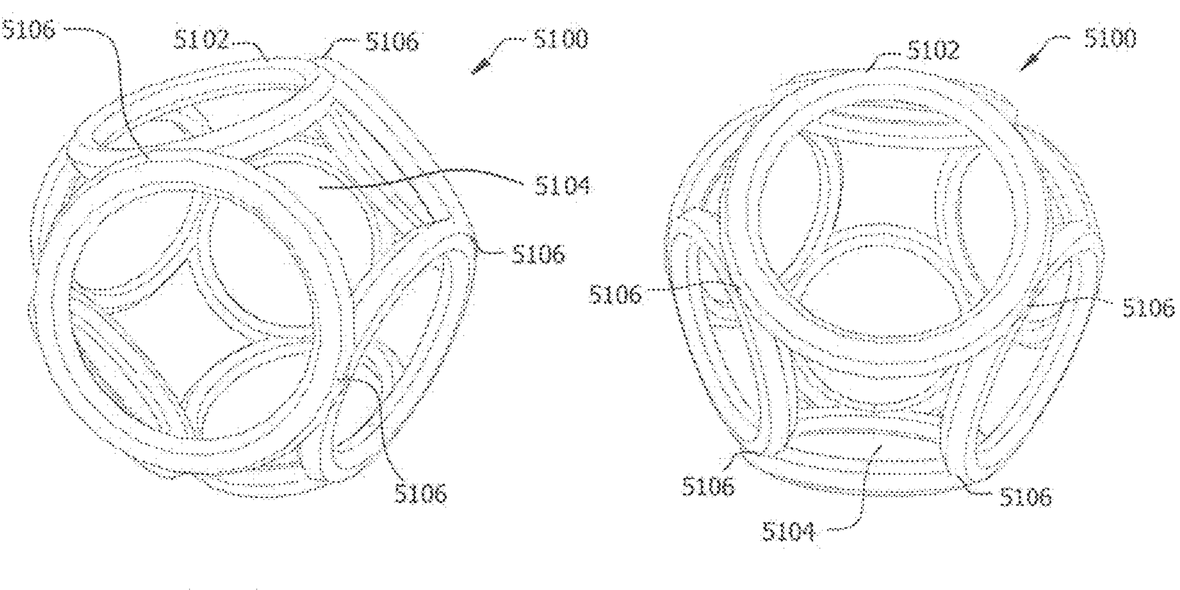
FIG. 51A
FIG. 51B
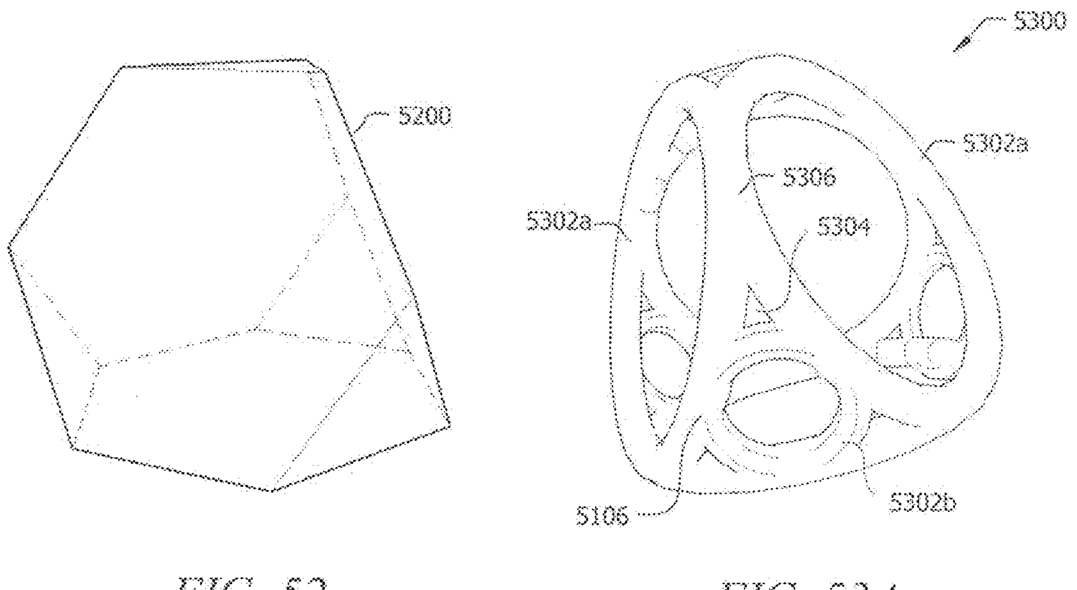
FIG. 52
FIG. 53A

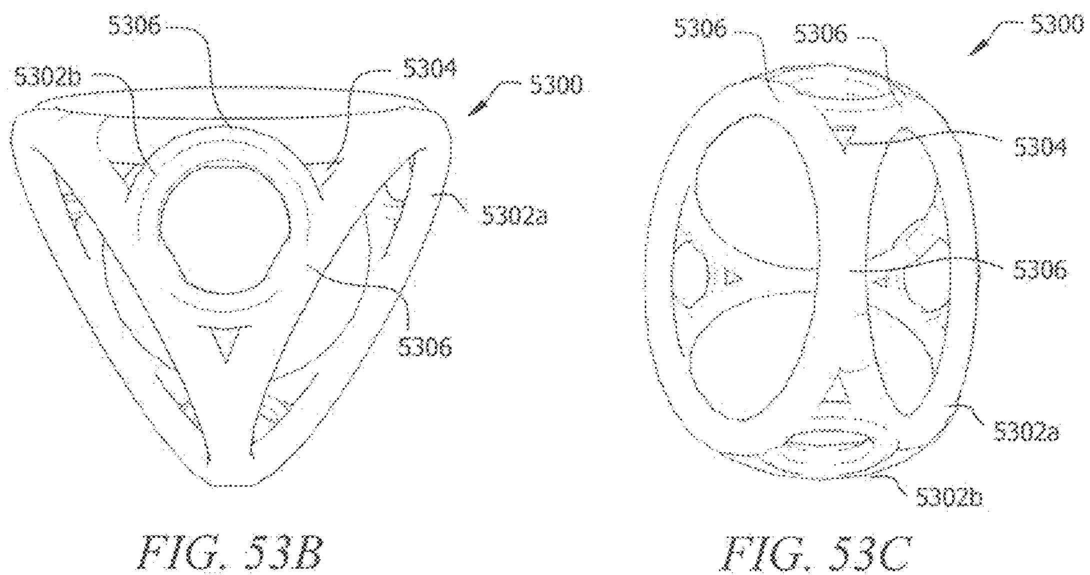
FIG. 53B
FIG. 53C
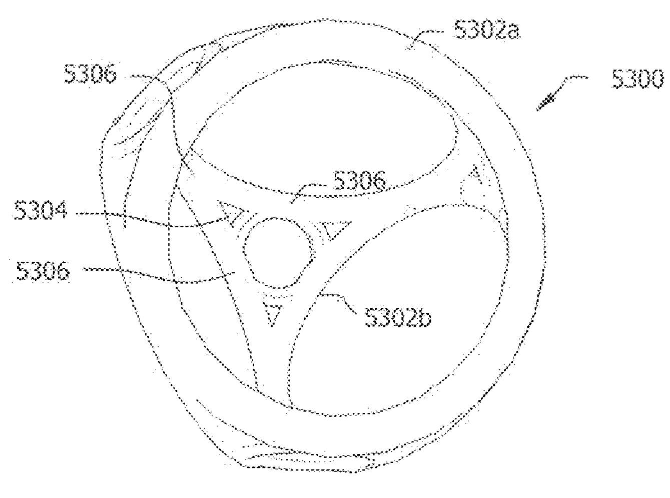
FIG. 53D

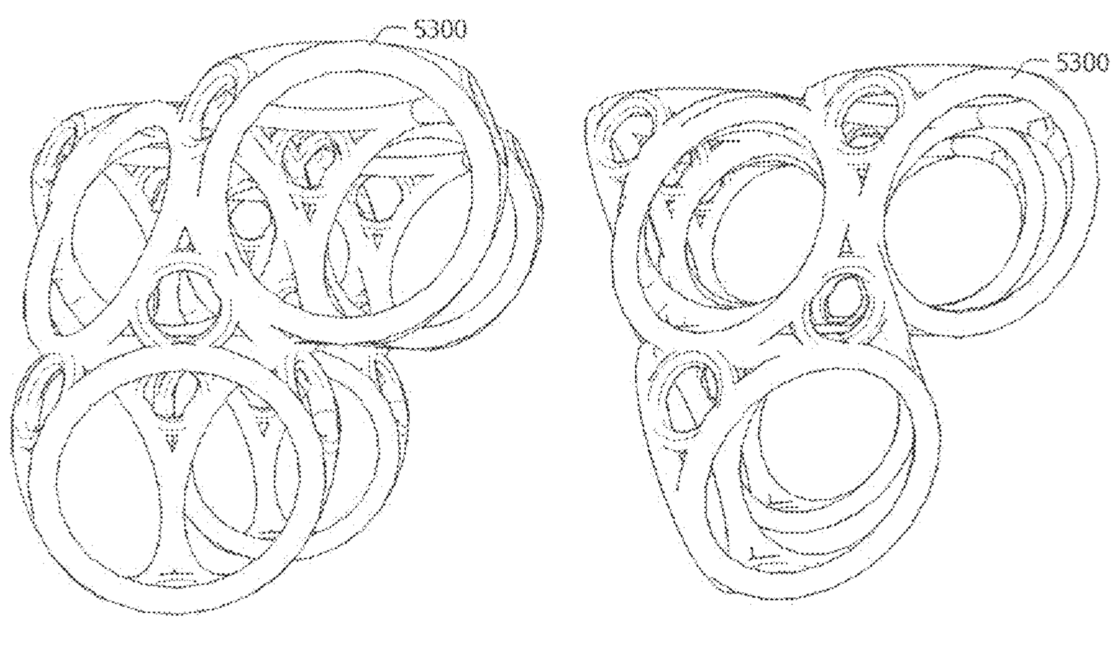
FIG. 54A
FIG. 54B
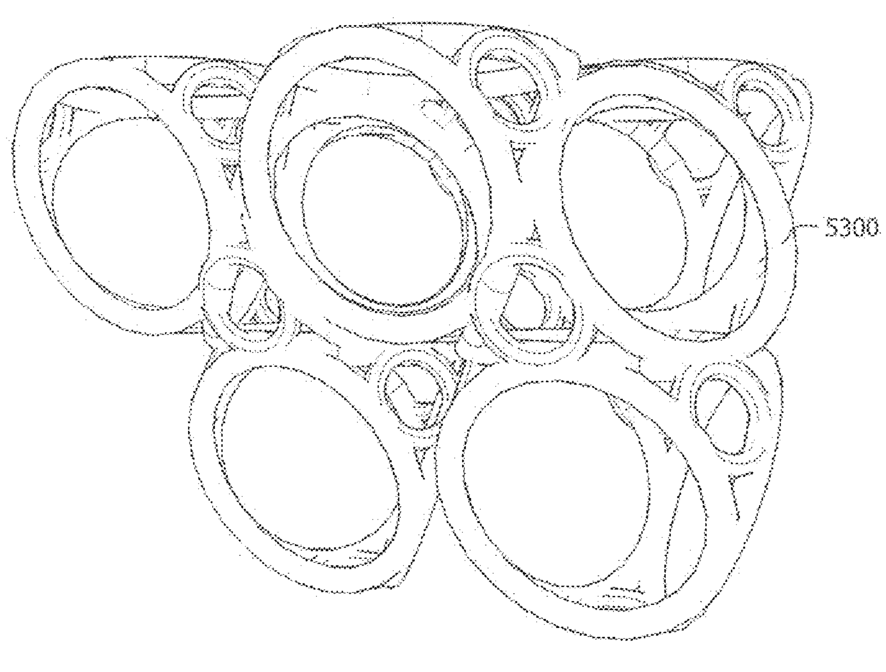
FIG. 54C

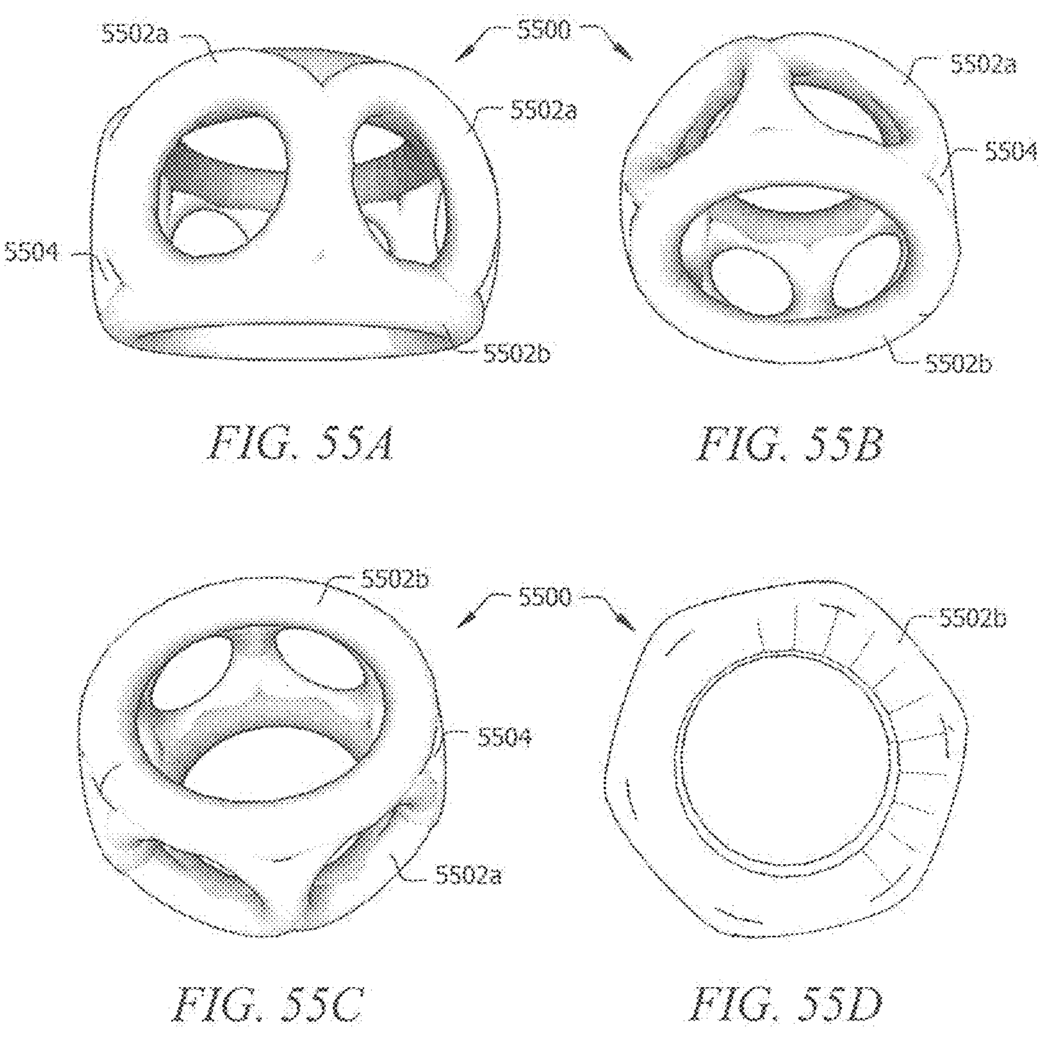
FIG. 55A
FIG. 55B
FIG. 55C
FIG. 55D
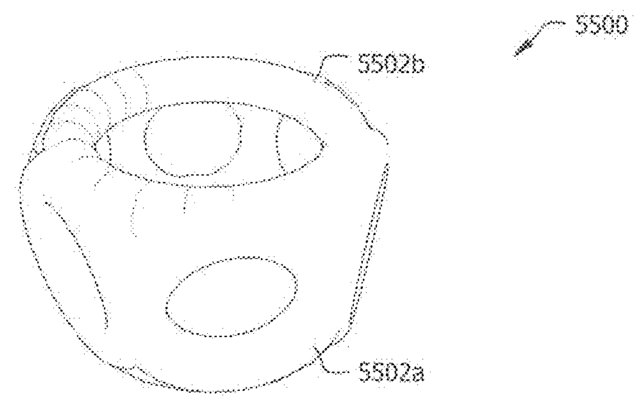
FIG. 55E

POROUS IMPLANT STRUCTURES

CROSS-REFERENCE TO RELATED APPLICATION

The present application is a continuation of U.S. patent application Ser. No. 18/370,685, filed Sep. 20, 2023, which is a continuation of U.S. patent application Ser. No. 17/988,003, filed Nov. 16, 2022, now issued U.S. Pat. No. 11,793,645, which is a continuation of U.S. patent application Ser. No. 17/158,397, filed Jan. 26, 2021, now issued U.S. Pat. No. 11,529,235, which is a divisional of U.S. patent application Ser. No. 15/603,936, filed May 24, 2017, now issued as U.S. Pat. No. 10,945,847, which is a divisional of U.S. patent application Ser. No. 13/391,126, filed May 2, 2012 and now issued as U.S. Pat. No. 9,668,863, which is a U.S. National Phase of International PCT Application No. PCT/US2010/046032, filed Aug. 19, 2010, which claims the benefit of U.S. Provisional Patent Application Ser. No. 61/235,269, filed Aug. 19, 2009, the contents of each application hereby incorporated by reference herein in their entirety.

FIELD OF THE INVENTION

The present invention generally relates to porous structures suitable for medical implants, and moss particularly to porous structures suitable for medical implants that have improved combinations of strength, porosity and connectivity and methods for fabricating such improved porous structures.

BACKGROUND

Metal foam structures are porous, three-dimensional structures with a variety of uses, including medical implants. Metal foam structures are suitable for medical implants, particularly orthopedic implants, because they have the requisite strength for weight bearing purposes as well as the porosity to encourage bone/tissue in-growth. For example, many orthopedic implants include porous sections that provide a scaffold structure to encourage bone in-growth during healing and a weight bearing section intended to render the patient ambulatory more quickly.

Metal foam structures can be fabricated by a variety of methods, For example, one such method Is mixing a powdered metal with a pore-forming agent (PFA) and then pressing the mixture into the desired shape. The PFA is removed using heal in a "burn out" process. The remaining metal skeleton may then be sintered to form a porous metal foam structure.

Another similar conventional method include applying a binder to polyurethane foam, applying metal powder to the binder, burning out the polyurethane foam and sintering the metal powder together to form a "green" part. Binder and metal powder are re-applied to the green part and the green part is re-entered until the green part has the desired strut thickness and porosity. The green part is then machined to the final shape and re-sintered.

While metal foams formed by such conventional methods provide good porosity, they may not provide sufficient strength to serve as weight bearing structures in many medical implants. Further, the processes used to form metal foams may lead to the formation of undesirable metal compounds in the metal foams by the reaction between the metal and the PFA. Conventional metal foam fabrication processes also consume substantial amounts of energy and may produce noxious fumes.

Rapid manufacturing technologies (RMT) such as direct metal fabrication (DMF) and solid free-form fabrication (SFF) have recently been used to produce metal foam used in medical implants or portions of medical implants. In general, RMT methods allow for structures to be built from 3-D CAD models. For example, DMF techniques produce three-dimensional structures one layer at a time from a powder which is solidified by irradiating a layer of the powder with an energy source such as a laser or an electron beam. The powder is fused, melted, or sintered, by the application of the energy source, which is directed in raster-scan fashion to selected portions of the powder layer. After fusing a pattern in one power layer, an additional layer of powder is dispensed, and the process is repeated with fusion taking place between the layers, until the desired structure is complete.

Examples of metal powders reportedly used in such direct fabrication techniques include two-phase metal powders of the copper-tin, copper-solder, and bronze-nickel systems. The metal structures formed by DMF may be relatively dense, for example, having densities of 70% to 80% of a corresponding molded metal structure, or conversely, may be relatively porous, with porosities approaching 80% or more.

While DMF can be used to provide dense structures strong enough to serve as weight bearing structures in medical implants, such structures do not have enough porosity to promote tissue and bone in-growth. Conversely, DMF can be used to provide porous structures having enough porosity to promote tissue and bone in-growth, but such porous structures lack the strength needed to serve as weight bearing structures. Other laser RMT techniques are similarly deficient for orthopedic implants requiring strength, porosity, and connectivity.

As a result of the deficiencies of metal foam implants and implants fabricated using conventional DMF methods, some medical implants require multiple structures, each designed for one or more different purposes. For example, because some medical implants require both a porous structure to promote bone and tissue in-growth and a weight bearing structure, a porous plug may be placed in a recess of a solid structure and the two structures may then be joined by sintering. Obviously, using a single structure would be preferable to using two distinct structures and sintering them together.

In light of the above, there is still a need for porous implant structures that provide both the required strength and desired porosity, particularly for various orthopedic applications. This disclosure provides improved porous structures that have both the strength suitable for weight bearing structures and the porosity suitable for tissue in-growth structures and a method for fabricating such improved porous structures.

SUMMARY OF THE INVENTION

One objective of the invention is to provide porous biocompatible structures suitable for use as medical implants that have improved strength and porosity.

Another objective of the invention is to provide methods to fabricate porous biocompatible structures suitable for use as medical implants that have improved strength and porosity.

To meet the above objectives, there is provided, in accordance with one aspect of the invention, a porous structure comprising: a plurality of struts, each strut comprises a first end, a second end; and a continuous elongated body between the first and second ends, where the body has a thickness and a length; and a plurality of nodes, each node comprises an intersection between one end of a first strut and the body of a second strut.

In a preferred embodiment, the first and second ends of one or more struts extend between the body of two other struts. In another preferred embodiment, the body of one or more struts comprise a plurality of nodes.

In accordance with another aspect of the invention, there is a porous structure comprising a plurality of struts, wherein one or more struts comprise a curved portion having a length and thickness; a plurality of junctions where two of said curved portions intersect tangentially; and a plurality of modified nodes, each modified node comprises an opening formed by three or more of said junctions.

In a preferred embodiment, the porous structure includes at least one strut comprising a straight portion having a length and a thickness. In another preferred embodiment, the porous structure includes at least one strut having a first end, a second end; and a continuous elongated body between the first and second ends, where the body has a thickness and a length; and at least one closed node comprising an intersection between one end of a first strut and the body of a second strut, wherein the strut can comprise of a straight portion, a curved portion, or both.

In accordance with another aspect of the invention, there are methods for fabricating a porous structure. One such method comprises the steps of: creating a model of the porous structure, the creation step comprises defining a plurality of struts and a plurality of nodes to form the porous structure and fabricating the porous structure according to the model by exposing metallic powder to an energy source. The defining step comprises the steps of providing a first end, a second end; and a continuous elongated body between the first and second ends for each strut, selecting a thickness a length for the body; and providing an intersection between one end of a first strut and the body of a second strut for each node.

In a preferred embodiment, the method includes defining the first and second ends of one or more struts extending between the body of two other struts. In another preferred embodiment, defining the body of one or more struts to comprise a plurality of nodes.

In accordance with another aspect of the invention, a second method for fabricating a porous structure comprises the steps of: creating a model of the porous structure: the creation step comprises selecting at least one frame shape and size for one or more cells of the porous structure, where the frame shape comprises a geometric shape selected from the group consisting of Archimedean shapes, Platonic shapes, strictly convex polyhedrons, prisms, anti-prisms and combinations thereof: adding one or more struts to the frame where the struts comprises a curved portion, said adding step is performed by inscribing or circumscribing the curved portion of the one or more struts within or around one or more faces of the selected shape; selecting a thickness for the frame and the one or more struts; and fabricating the porous structure according to the model by exposing metallic powder to an energy source.

In a preferred embodiment, the creation step includes the step of removing a portion of the frame from one or more cells of the model. In another preferred embodiment, the fabrication step includes defining $N_{(1, x)}$ layer-by-layer patterns for the porous structure based on the selected dimensions, at least one cell shape and at least one cell size, where N ranges from 1 for the first layer at a bottom of the porous structure to x for the top layer at a top of the porous structure; depositing an $N^{th}$ layer of powdered biocompatible material; fusing or sintering the $N^{th}$ pattern in the deposited $N^{th}$ layer of powdered biocompatible material; and repeating the depositing and fusing or sintering steps for N=1 through N=X.

In a refinement, the method may further comprise creating a model of the porous structure wherein, for at least some nodes, no more than two struts intersect at the same location.

In another refinement, the method may comprise creating a model of the porous structure wherein at least one strut or strut portion is curved.

The disclosed porous structures may be fabricated using a rapid manufacturing technologies such as direct metal fabrication process. The struts can be sintered, melted, welded, bonded, fused, or otherwise connected to another strut. The struts and nodes can define a plurality of fenestrations. Further, the struts and nodes can be fused, melted, welded, bonded, sintered, or otherwise connected to one another to form a cell, which can be fused, melted, welded, bonded, sintered, or otherwise connected to other cells to form a continuous reticulated structure.

In some refinements, at least one, some, or all struts of a cell may have a uniform strut diameter. In some refinements, one, some, or all of the struts of a cell may have a non-uniform strut diameter. In some refinements, a cell may have combinations of struts having uniform and non-uniform strut diameters. In some refinements, at least one, some, or all of the uniform diameter struts of a cell may or may not share similar, different, or identical strut diameters, longitudinal shapes, cross-sectional shapes, sizes, shape profiles, strut thicknesses, material characteristics, strength profiles, or other properties. In some refinements, one, some, or all struts within a cell may grow or shrink in diameter at similar, different, or identical rates along a predetermined strut length.

In some refinements, struts within a cell may extend between two nodes. In a further refinement of this concept, struts may have varying cross-sectional diameters along a strut length, including a minimum diameter at a middle portion disposed between the two nodes. In further refinement of this concept, struts may have two opposing ends, with each end connected to a node and a middle portion disposed between the two ends. Struts may flare or taper outwardly as they extend from the middle portion towards each node so that a diameter of the middle portion is generally smaller than a diameter of either or both of the two opposing ends. In some instances, the struts may flare in a parabolic fluted shape or may taper frusto-conically.

In other refinements, at least one, some, or all struts within a cell are curved. In further refinement of this concept, one, some, or all of the cells within a porous structure comprise at least one curved strut. In further refinement of this concept, all of the struts that make up a porous structure are curved. In further refinement of this concept, curved struts may form complete rings or ring segments. The rings or ring segments may be inter-connected to form open sides or fenestrations of multiple-sided cells. In some instances, a single ring may form a shared wall portion which connects two adjacent multiple-sided cells. In some instances, one or more ring segments alone or in combination with straight strut portions may form a shared wall portion which connects two adjacent multiple-sided cells. In still a further refinement, the number of sides of each cell may range from about 4 to about 24. More preferably, the number of sides of each cell may range from about 4 to about 16. One geometry that has been found to be particularly effective is a dodecahedron or 12 sided cell. However, as explained and illustrated below, the geometries of the individual cells or the cells of the porous structure may vary widely and, in the geometries, may vary randomly front cell to cell of a porous structure.

In another refinement, the configurations of the cells, struts, nodes and/or junctions may vary randomly throughout the porous structure to more closely simulate natural bone tissue.

In another refinement, each cell may be multiple-sided and having an overall shape that may fit within a geometric shape selected from the group consisting of tetrahedrons, truncated tetrahedrons, cuboctahedrons, truncated hexahedrons, truncated octahedrons, rhombicuboctahedrons, truncated cuboctahedrons, snub hexahedrons, snub cuboctahedrons, icosidodecahedrons, truncated dodecahedrons, truncated icosahedrons, rhombicosidodecahedrons, truncated icosidodecahedrons, snub dodecahedrons, snub icosidodecahedrons, cubes, octahedrons, dodecahedrons, icosahedrons, prisms, prismatoids, antiprisms, uniform prisms, right prisms, parallelepipeds, cuboids, polytopes, honeycombs, square pyramids, pentagonal pyramids, triangular cupolas, square cupolas, pentagonal cupolas, pentagonal rotundas, elongated triangular pyramids, elongated square pyramids, elongated pentagonal pyramids, gyroelongated square pyramids, gyroelongated pentagonal pyramids, triangular dipyramids, pentagonal dipyramids, elongated triangular dipyramids, elongated square dipyramids, elongated pentagonal dipyramids, gyroelongated square dipyramids, elongated triangular cupolas, elongated square cupolas, elongated pentagonal cupolas, elongated pentagonal rotundas, gyroelongated triangular cupolas, gyroelongated square cupolas, gyroelongated pentagonal cupolas, gyroelongated pentagonal rotundas, gyrobifastigium, triangular orthobicupolas, square orthobicupolas, square gyrobicupolas, pentagonal orthobicupolas, pentagonal gyrobicupolas, pentagonal orthocupolarotundas, pentagonal gyrocupolarotundas, pentagonal orthobirotundas, elongated triangular orthobicupolas, elongated triangular gyrobicupolas, elongated square gyrobicupolas, elongated pentagonal orthobicupolas, elongated pentagonal gyrobicupolas, elongated pentagonal orthocupolarotundas, elongated pentagonal gyrocupolarotundas, elongated pentagonal orthobirotundas, elongated pentagonal gyrobirotundas, gyroelongated triangular bicupolas, gyroelongated square bicupolas, gyroelongated pentagonal bicupolas, gyroelongated pentagonal cupolarotundas, gyroelongated pentagonal birotundas, augmented triangular prisms, biaugmented triangular prisms, triaugmented triangular prisms, augmented pentagonal prisms, biaugmented pentagonal prisms, augmented hexagonal prisms, parabiaugmented hexagonal prisms, metabiaugmented hexagonal prisms, triaugmented hexagonal prisms, augmented dodecahedrons, parabiaugmented dodecahedrons, metabiaugmented dodecahedrons, triaugmented dodecahedrons, metabidiminished icosahedrons, tridiminished icosahedrons, augmented tridiminished icosahedrons, augmented truncated tetrahedrons, augmented truncated cubes, biaugmented truncated cubes, augmented truncated dodecahedrons, parabiaugmented truncated dodecahedrons, metabiaugmented truncated dodecahedrons, triaugmented truncated dodecahedrons, gyrate rhombicosidodecahedrons, parabigyrate rhombicosidodecahedrons, metabigyrate rhombicosidodecahedrons, trigyrate rhombicosidodecahedrons, diminished rhombicosidodecahedrons, paragyrate diminished rhombicosidodecahedrons, metagyrate diminished rhombicosidodecahedrons, bigyrate diminished rhombicosidodecahedrons, parabidiminished rhombicosidodecahedrons, metabidiminished rhombicosidodecahedrons, gyrate bidiminished rhombicosidodecahedrons, and tridiminished rhombicosidodecahedrons, snub disphenoids, snub square antiprisms, sphenocorons, augmented sphenocoronas, sphenomegacoroma, hebesphenomegacorona, disphenocingulum, bilunabirotundas, triangular hebesphenorotundas, and combinations thereof.

In another refinement, the powder is selected from the group consisting of metal, ceramic, metal-ceramic (cermet), glass, glass-ceramic, polymer, composite, and combinations thereof.

In another refinement, the metallic material is selected from the group consisting of titanium, titanium alloy, zirconium, zirconium alloy, niobium, niobium alloy, tantalum, tantalum alloy, nickel-chromium (e.g., stainless steel), cobalt-chromium alloy and combinations thereof.

In another refinement, the porous structure forms at least a portion of a medical implant, such as an orthopedic implant, dental implant, or vascular implant.

Porous orthopedic implant structures for cell, and tissue in-growth and weight bearing strength are also disclosed that may be fabricated using a near-net shape manufacturing process such as a direct metal fabrication (DMF) process for use with metallic biomaterials or a stereo-lithography manufacturing process for use with polymeric biomaterials. In instances where a DMF process is utilized, a powdered biocompatible material is provided in layers and individual particles of one layer of powdered biocompatible material are fused or sintered together one layer at a time. Exemplary porous structures comprise a plurality of three-dimensional cells. Each cell comprises a plurality of struts. Each strut may be sintered or fused to one other strut at a node. Each node may comprise a junction of not more than two struts. The struts and nodes of each cell define a plurality of fenestrations. Each cell comprises from about 4 to about 24 fenestrations. At least one strut of at least some of the cells are curved. Each cell may be fused or sintered to at least one other cell to form a continuous reticulated structure.

Other advantages and features will be apparent from the following detailed description when read in conjunction with the attached drawings. The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention reference is now made to the following descriptions taken in conjunction with the accompanying drawing, in which:

FIGS. 1A-1B illustrate 3-D representations of an example of the struts at a node in a porous structure of the prior art where the struts of FIG. 1A have like diameters and the struts of FIG. 1B have different diameters.

FIG. 2 is a SEM (Scanning Electron Microscope) microphotograph of an example of fractured struts of the prior art.

FIGS. 13A-13M illustrate 2-D representations of various exemplary configurations of the frame of the two struts of the present invention forming a node, including frames for struts that are straight curved, or a combination of both.

FIGS. 24A and 24B illustrate various views of 3-D representations of a conventional cell of the porous structure of the prior art based on a dodecahedral shape.

FIGS. 25A and 25B illustrate various views of 3-D representations of one embodiment of a cell of the porous structure of the present invention also based on a dodecahedral shape.

FIG. 29B is a partial view of a 3-D representation of the frame of the cell.

FIGS. 37A and 37B illustrate various views of 3-D representations of another embodiment of a cell of the present invention based on a dodecahedral shape.

FIG. 38 illustrates a 3-D representation of yet another embodiment of a cell of the present invention based on a dodecahedral shape.

FIGS. 39A-39C illustrate various views of 3-D representations of yet another embodiment of a cell of the present invention based on a dodecahedral shape.

FIG. 40 illustrates a 3-D representation of an exemplary arrangement of the cells of FIGS. 24 and 25.

FIGS. 41A and 41B illustrate various views of 3-D representations of an exemplary arrangement of the cells of FIGS. 24, 25, and 37.

FIG. 43 illustrates a 3-D representation of an exemplary arrangement of the present invention of cells based on truncated octahedra.

FIG. 44 illustrates a 3-D representation of an exemplary arrangement of the present invention of cells based on cubes (light grey), truncated cuboctahedra (black), and truncated octahedra (dark grey).

FIG. 45 illustrates a 3-D representation of an exemplary arrangement of the present invention of cells based on cuboctahedra (black), truncated octahedra (dark grey) and truncated tetrahedra (light grey).

FIGS. 48-50 illustrate 3-D representations of a frame based on octahedron modified by one embodiment of the present invention.

FIGS. 51A and 51B illustrate various views of 3-D representations of a cell of the present invention formed from the frames of FIGS. 48-50.

FIG. 52 illustrates a 3-D representation of a frame based a truncated tetrahedron.

FIGS. 53A-53D Illustrate various views of 3-D representations of a cell formed from the frame of FIG. 52 that was modified by one embodiment of the present invention.

FIGS. 54A-54E illustrate various views of 3-D representations of an exemplary arrangement of the cells of FIG. 53.

FIGS. 55A-55E illustrate 3-D representations of a cell formed from a frame based on a hexagonal prism that was modified by one embodiment of the present invention.

FIGS. 56A-56B and 57A-57B illustrate 3-D representations of an exemplary arrangement of the cells of FIG. 55.

Figures 3, 4, 5, 6, 7, 8:
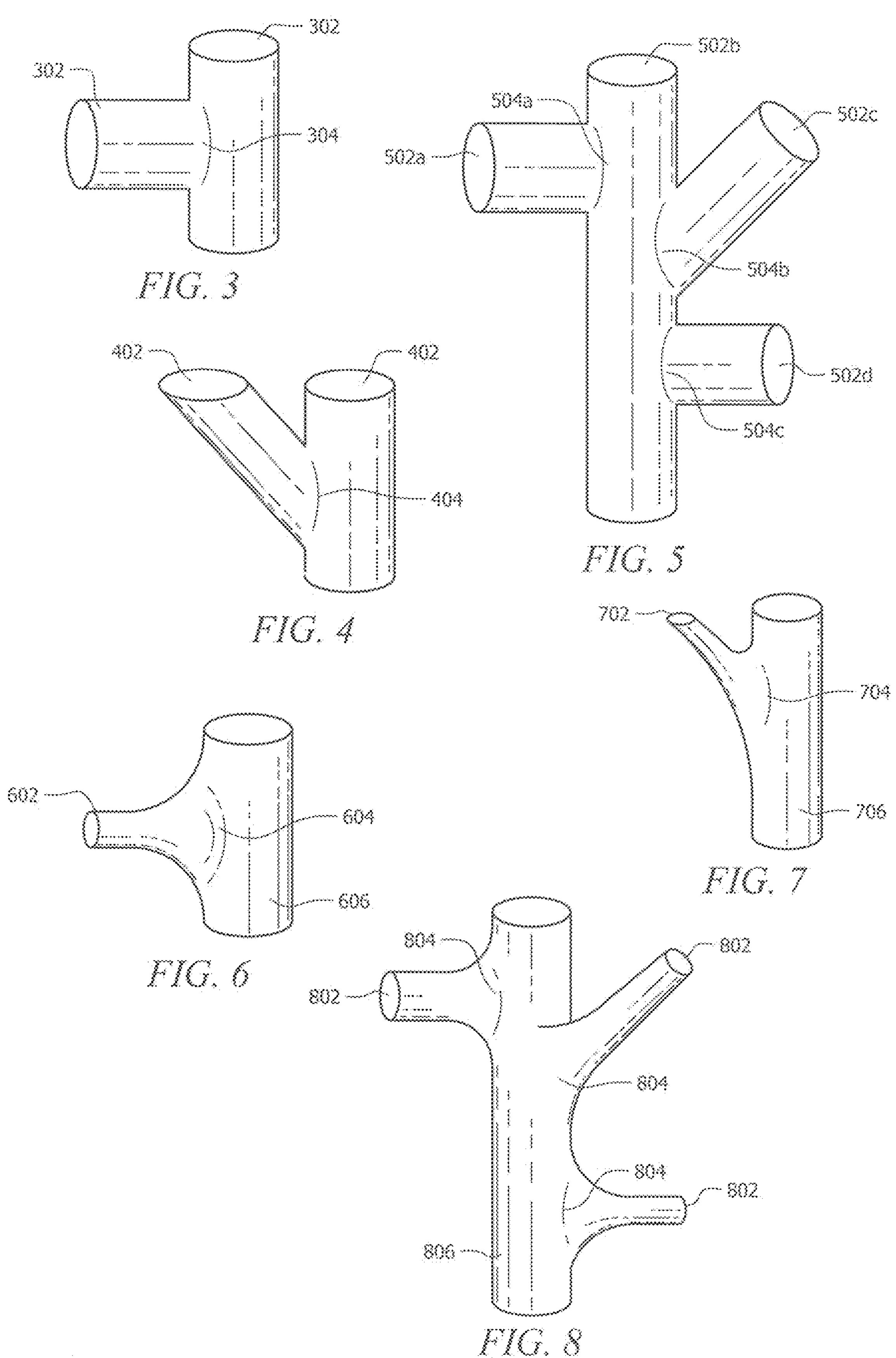
FIGS. 3-5 illustrate 3-D representations of one embodiment of the struts and nodes of the present invention.
FIGS. 6-8 illustrate 3-D representations of another embodiment of the struts and nodes of the present invention where at least some of the struts comprises a smaller cross-sectional diameter at the body portion of the strut as compared to the cross-sectional diameter at the node.

It should be understood that the drawings are not necessarily to scale and that the disclosed embodiments are sometimes illustrated diagrammatically and in partial views. In certain instances, details which are not necessary for an undemanding of the disclosed methods and apparatuses or which render other details difficult to perceive may have been omitted. Also, for simplification purposes, there may be only one exemplary instance, rather than all, is labeled. It should be understood, of course, that this disclosure is not limited to the particular embodiments illustrated herein.

DETAILED DESCRIPTION OF INVENTION

As discussed, above, Rapid Manufacturing Techniques (RMT) such as Direct Metal Fabrication (DMF) can be used to produce porous structures for medical implants. However, using DMF or other RMT to fabricate porous structures can create weak areas between fenestrations of the three-dimensional porous structure. This is mostly due to the shapes and configurations of the cells that have been used in the prior art to form these porous structures. In particular, fractures typically occur at areas where struts are connected together at a node. The fractures occur in porous structures of the prior art because the cross-sectional area of a strut where it connects to the node is typically less than the cross-sectional area of the resulting node. The areas where the struts connect to their node, typically referred to as stress risers, are common points of structural failure. The pattern of failure at the stress risers can also occur when the molten phase of particles does not completely melt and fuse together or when the surrounding substrate surfaces is too cold, which causes the hot powdered material to bead up during the DMF process. Regardless of the exact causes of strut fractures and the resulting poor performance of porous structures of the prior art, improved porous structures that can be fabricated using RMT, including DMF, and other free-form fabrication and near net-shape processes (e.g., selective laser sintering, electron beam melting, and stereo-lithography) are desired.

FIGS. 1A and 1B provide an illustration of where fractures may occur. FIGS. 1A-1B illustrate an example of a porous structure with three or four struts, respectively, connected at a single node, where the struts of FIG. 1A have the same diameters and the struts of FIG. 1B have different diameters. Specifically, in FIG. 1A, three struts 102 of generally equal diameters are connected together at node 104. Three stress risers 106 are created at the connections between the three struts 102. Because the cross-sectional diameters of struts 102 at the stress risers 106 are less than the cross-sectional diameter of the node 104, the stress risers 106 are locations for a typical strut failure. In FIG. 1B, three smaller struts 108 are connected to a larger strut 110 at a node 112. Three of the four resulting stress risers are shown at 114, which have substantially smaller cross-sectional diameters than the node 112. FIG. 2 is a SEM (Scanning Electron Microscope) microphotograph of a structure 200 fabricated using RMT, and it shows an example of strut fracture surfaces 202. In FIG. 2, the sample shown is occluded with build powder 204 in the areas around the strut fracture surfaces 202.

Referring to FIGS. 3-5, various embodiments of the present invention are shown. In FIGS. 3-5, struts 302, 402, and 502 are connected together at their respective nodes 304, 404, and 504 in various combinations. Each of nodes 304, 404, and 504 is a connection between only two struts. For example, in FIG. 5, node 504*a* comprises a connection between struts 502*a* and 502*b*; node 504*b* comprises a connection between struts 502*b* and 502*c*; and node 504*c* comprises a connection between struts 502*b* and 502*d*. By reducing the number of struts 302, 402, and 502 that meet or are connected at their respective nodes 304, 404, and 504, the diameter or cross-sectional area where the struts 302, 402, and 502 are connected is substantially equal to the cross-sectional area at the respective nodes 304, 404, and 504. Therefore, the effect of the stress risers (not shown) on the strength of the structure is lessened in the structures illustrated in FIGS. 3-5. Consequently, the resulting structures are substantially stronger than the structures of the prior art illustrated in FIGS. 1A-1B.

FIGS. 6-8 illustrate alternative embodiments of the porous structures of the present invention comprising strut and node combinations where at least some of the struts are characterized by a smaller cross-sectional diameter at the body of the strut than at the stress riser. The struts 602, 702, and 802 are characterized by a fluted or conical shape where each of struts 602, 702, and 802 flares to a wider cross-sectional diameter as the strut approaches and connects at the respective nodes 604, 704, and 804. The designs of FIGS. 6-8 illustrate incorporate fluted struts 602, 702, and 802 and non-fluted struts 606, 706, and 806, where both types of struts are connected at the respective nodes 604, 704, and 804.

Figure 9A:
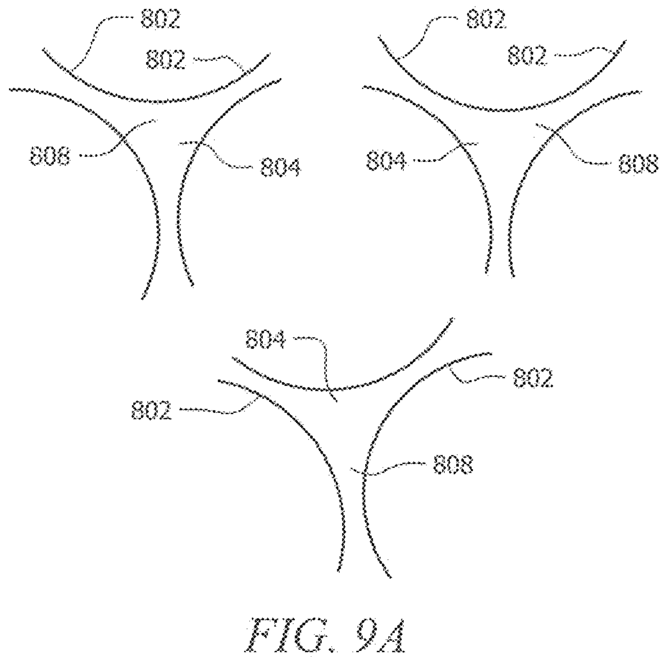
FIGS. 9A and 9B illustrate plan views of the embodiments in FIGS. 6-8.
Figure 9B:
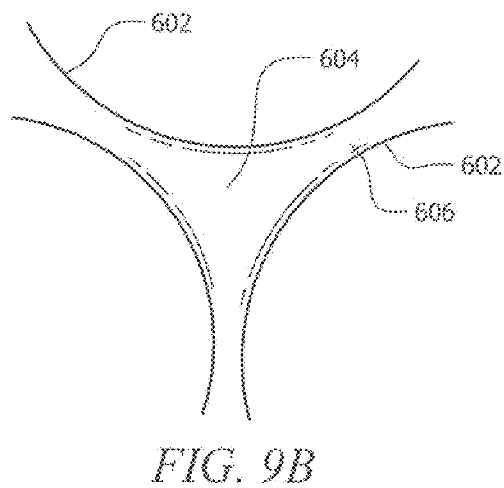
Figures 10A, 10B, 10C, 11A, 11B, 11C:
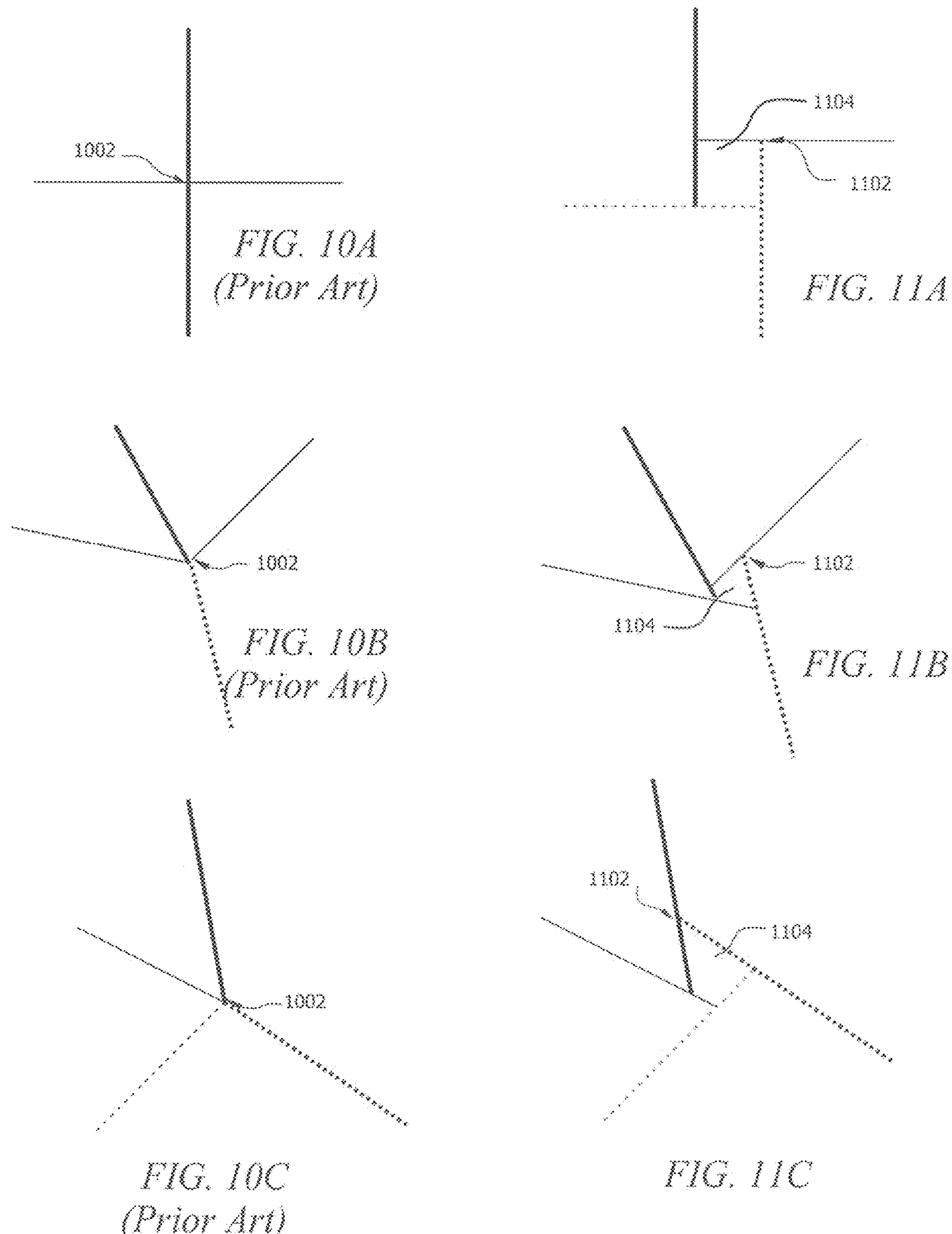
FIGS. 10A-10F illustrate 2-D representations of various configurations of the frame of struts and nodes in a porous structure of the prior art.
FIGS. 11A-11F illustrate 2-D representations of the corresponding configurations of the frame of struts and nodes of the prior art in FIGS. 10A-10F modified by one embodiment of the present invention.
Figures 10D, 10E, 10F, 11D, 11E, 11F:
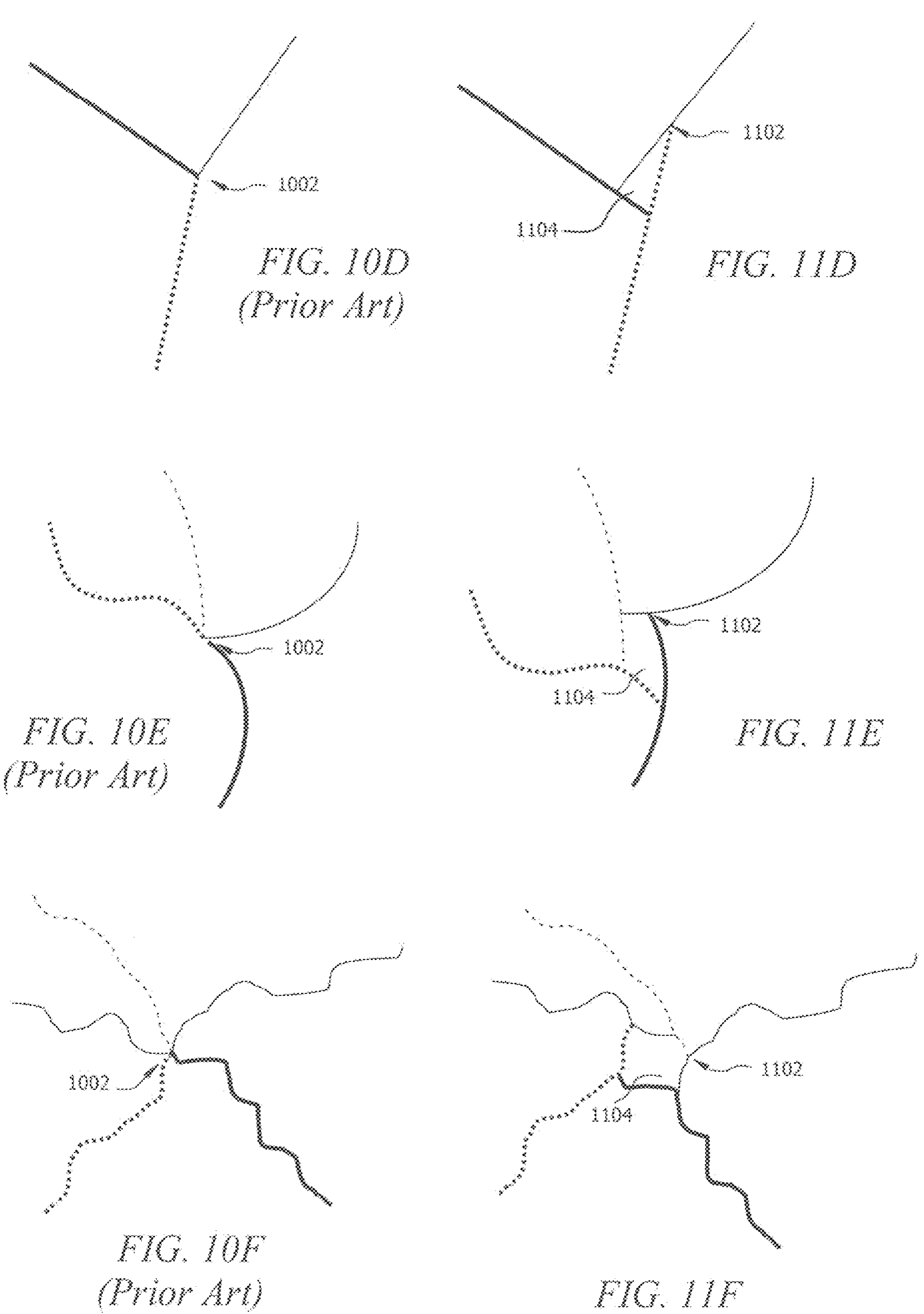
Figures 12A, 12B:
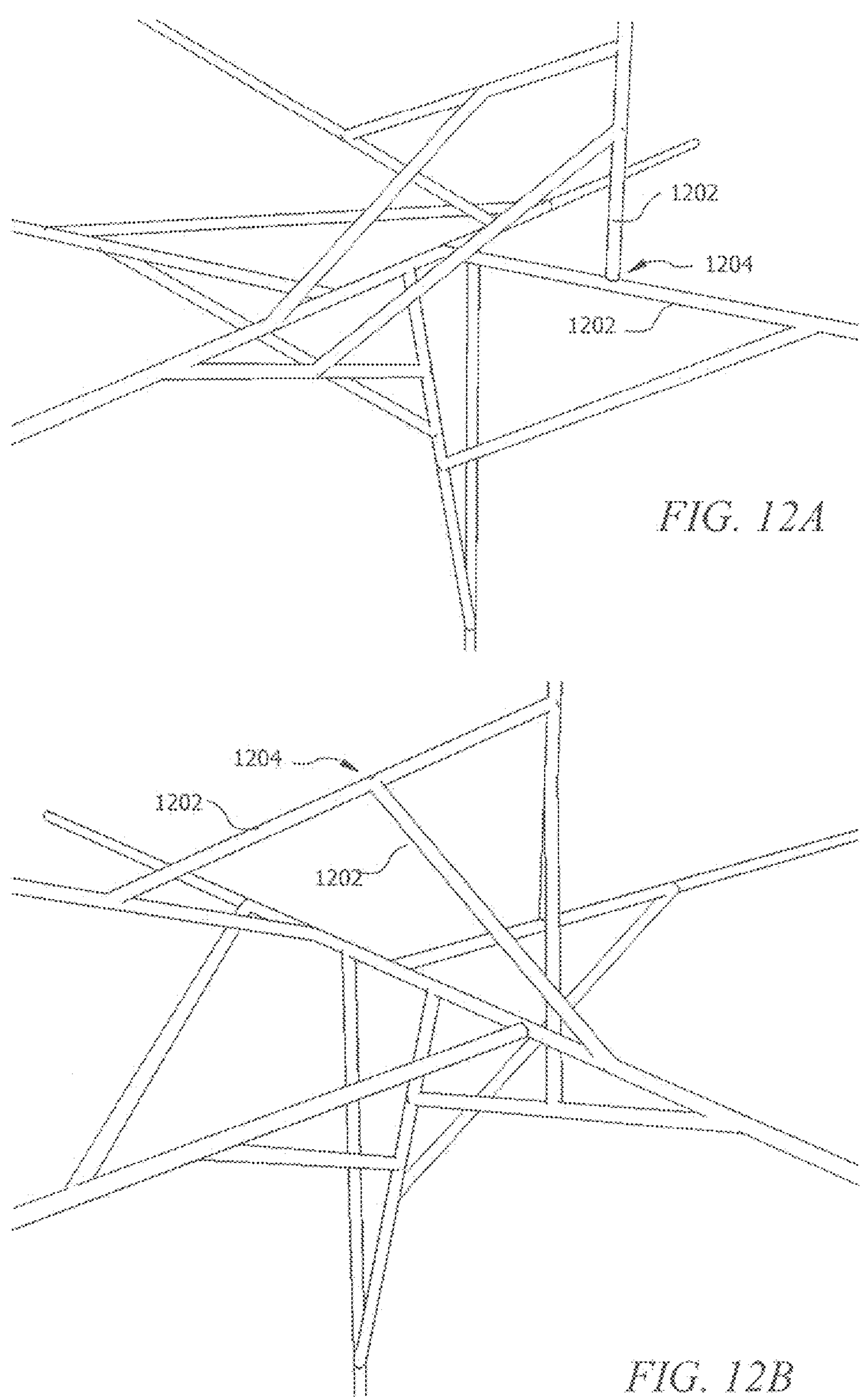
FIGS. 12A-12D illustrate 3-D representations of exemplary embodiments of the porous structure of the present invention comprising one or more frame configurations in FIGS. 11A-11F.
Figures 12C, 12D:
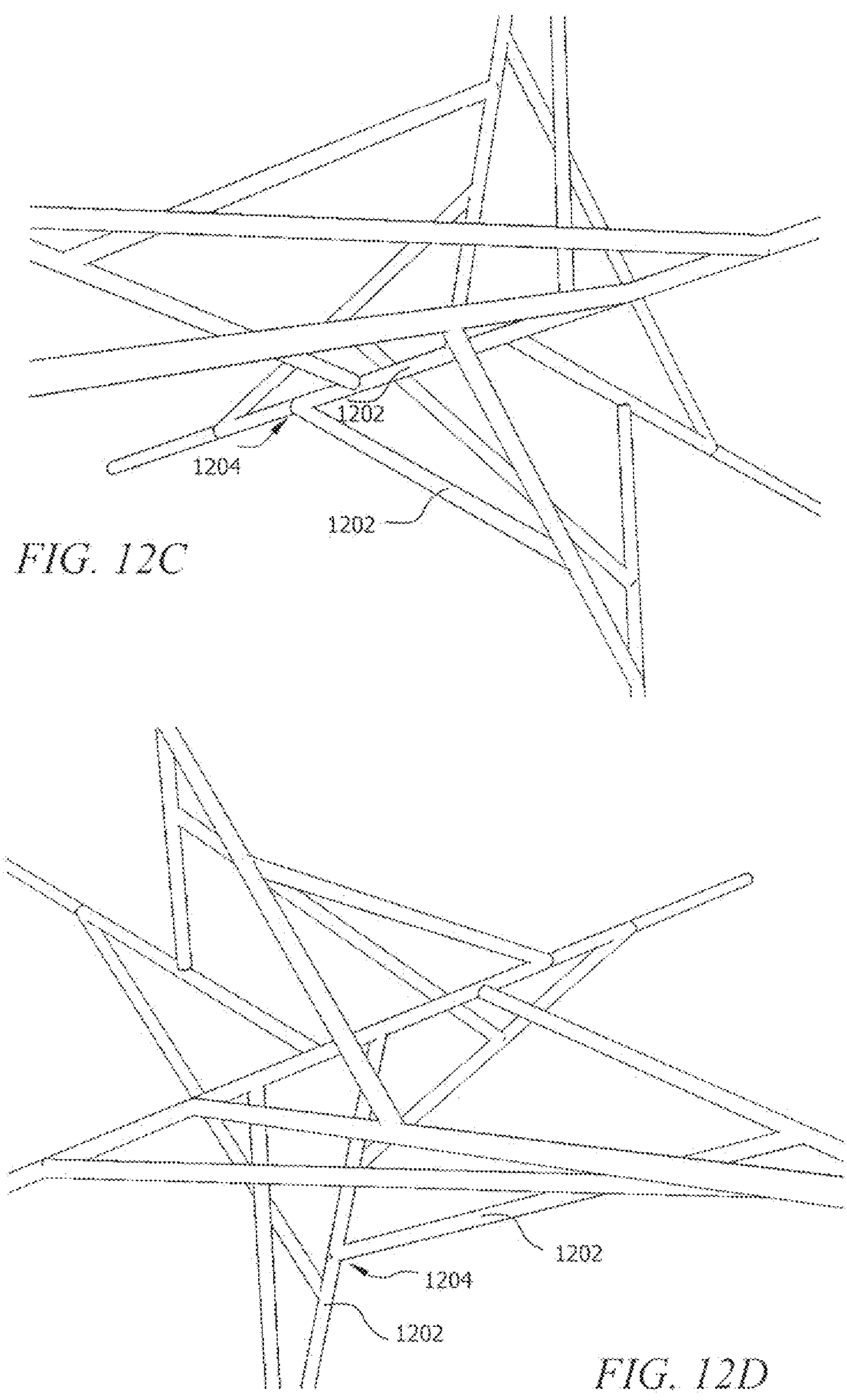

Thus, each of the connections between the fluted struts 602, 702, and 802 and the non-fluted struts 606, 706, and 806 has a cross-sectional diameter that is essentially equivalent to the maximum cross-sectional diameter of fluted struts 602, 702, and 802. Accordingly, the effect of the stress risers (not shown) of the structures are thereby reduced. Referring to FIG. 9A, it is a plan view of the struts 802 and nodes 804 in FIG. 8. FIG. 9B is a plan view of an individual node in FIGS. 6-8, which is labeled as struts 602 and node 604 for demonstrative purposes. Referring to FIGS. 9A-9B, the fluted struts 602, 802 have a larger or maximum cross-sectional diameter at the ends 606, 806 that meet at the nodes 804, 604, and a smaller or minimum cross-sectional diameter at the middle portions. Thus, the effect of stress risers (not shown) at the junctions between the struts fluted struts 602, 702, and 802 and the non-fluted struts 606, 706, and 806 are reduced. Preferably, only two struts, e.g., 602 and 606, meet any given node, e.g. 604, for added strength.

FIGS. 10A-10F illustrate 2-D representations of various configurations of the frame of the struts and nodes in a porous structure of the prior art. For simplification purposes, the struts are not represented in 3-D but rather each strut is represented by a different line, e.g., its frame, that is either solid, bolded solid, or dashed lines. This representation is simply exemplary and not meant to be limiting. In the prior art, it is typical for a porous structure to have more than two struts meeting at a node 1002, regardless whether the strut may be straight, curved, or irregular. While FIG. 10A may show two struts meeting at a node, the stress risers of this configuration has the effect of the stress risers at a node with four struts connecting or intersecting one another. For example, U.S. Publication Nos. 2006/0147332 and 2010/0010638 show examples of these prior art configurations employed to form porous structures.

In contrast, to the prior art configurations of FIGS. 10A-10F, the present invention reduces the effect of the stress risers at the nodes by ensuring that no more than two struts intersect at a node. Consequently, some embodiments result in the diameter or cross-sectional area where the struts intersect being substantially equal to the cross-sectional area at each node, thereby reducing the effect of the stress risers on the strength of the structure. FIGS. 11A-11F illustrate exemplary embodiments of the present invention for modifying the corresponding configuration of the prior art to ensure that no more than two struts intersect at a node. As seen in FIGS. 11A-11F, each of the nodes 1102 has only two struts intersecting. For simplification purposes, only one of the numerous nodes in 11A-11F is labeled with the number 1102. In particular, the FIGS. 11A-11F show at nodes 1102, the end of one strut intersect the body of another strut. Further, the modification of the prior art configurations according to one embodiment of the present invention forms a modified pore 1104 that is open in each configuration that provides additional porosity with added strength, which is a great improvement over the prior art. FIGS. 12A-12D illustrate 3-D representations of exemplary embodiments of the porous structure of the present invention formed with one or more configurations in FIGS. 11A-11F, where the frames, e.g., lines, have been given a thickness to form struts. In FIGS. 12A-12D, the porous structures have struts 1202 that intersect one another at nodes 1204 where no more than two nodes intersect at a node.

As demonstrated by FIGS. 11A-11F, the conventional nodes 1002 of FIGS. 10A-10F are effectively being "opened" up to ensure that no more than two struts meet at a node. In addition to reducing the effect of stress risers at the node, this "opening" up of the conventional nodes 1002 of FIGS. 10A-10F into nodes 1102 of FIGS. 11A-11F has the added benefit of reducing heat variations during the fabrication process. As with any other thermal processes, being able to control the heat variations, e.g., cooling, of the material is important to obtain the desired material properties.

Figures 13A, 13B, 13C:
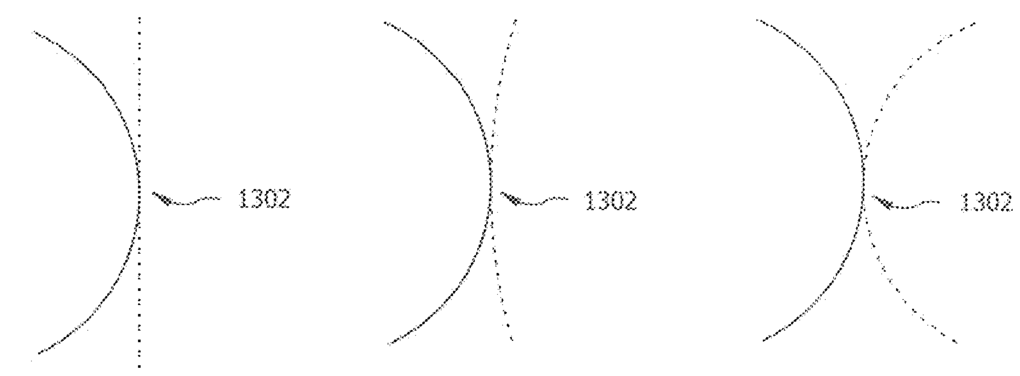
Figures 13D, 13E, 13F:
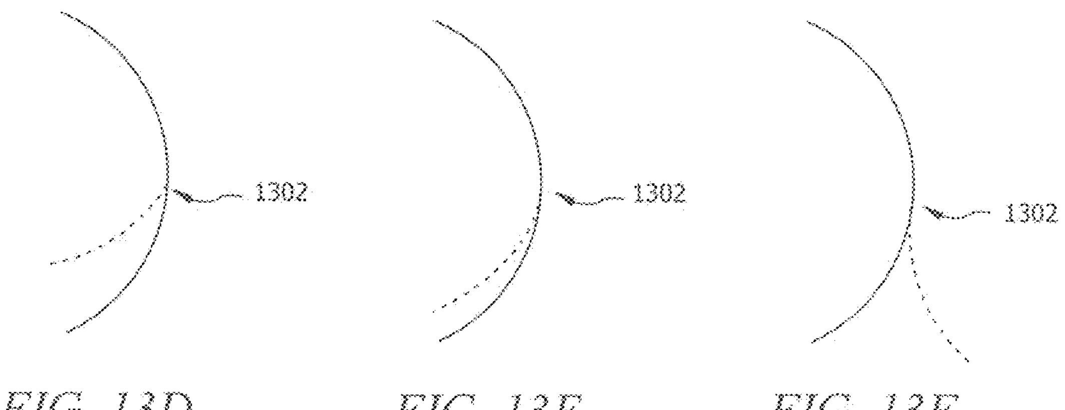
Figures 13G, 13H, 13I:
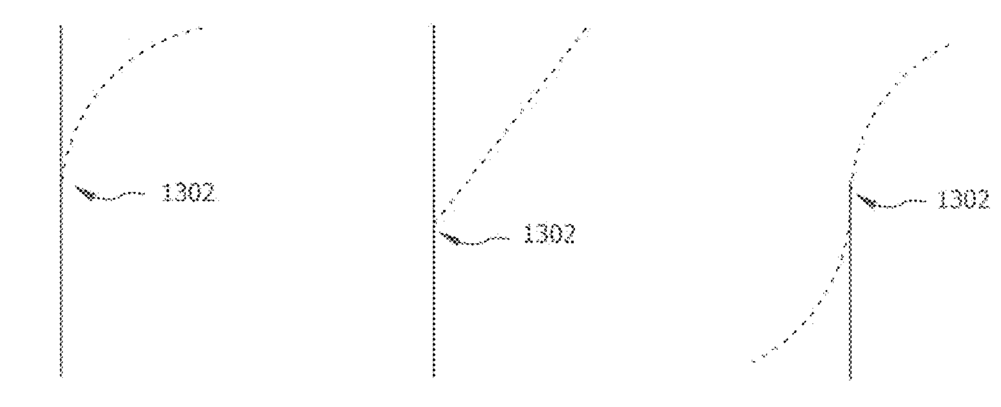
Figures 14, 15A, 15B:
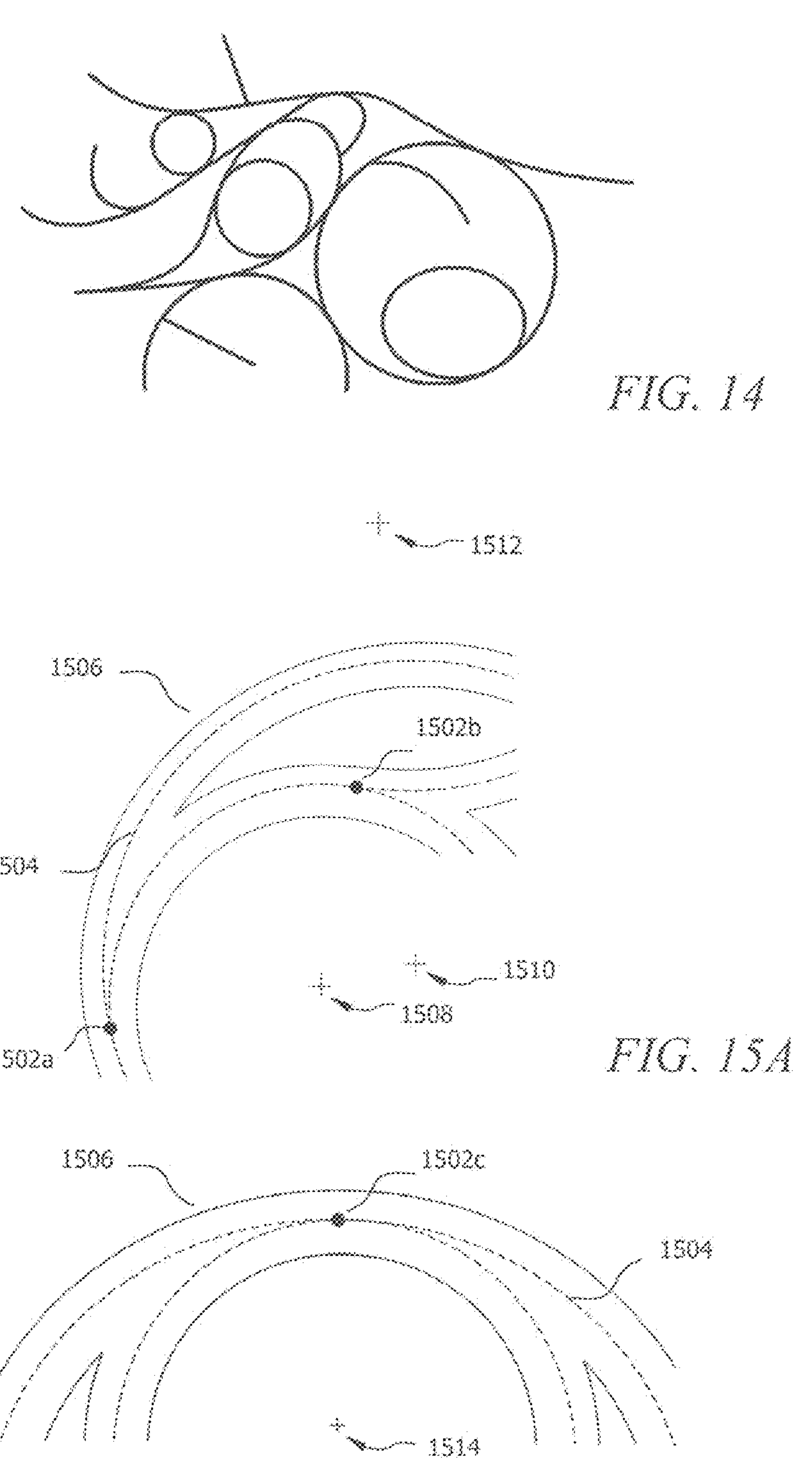
FIG. 14 illustrates a 2-D representation of an exemplary embodiment of the porous structure of the present invention comprising one or more frame configurations in FIGS. 13A-13M.
FIGS. 15A-15C illustrate 2-D representations of exemplary configurations of various curved frames and corresponding struts of the present invention intersecting to form a node.
Figure 15C:
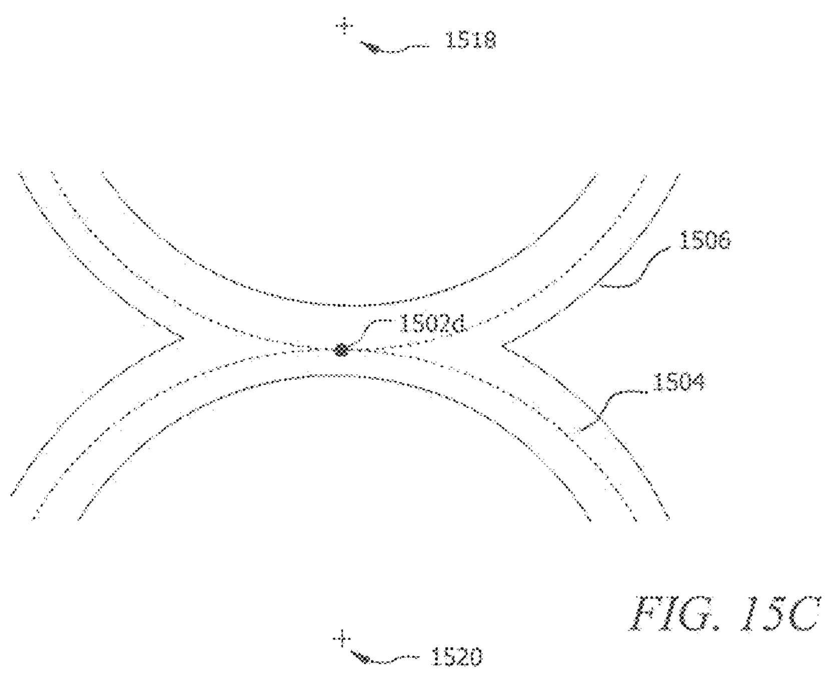
Figure 16:
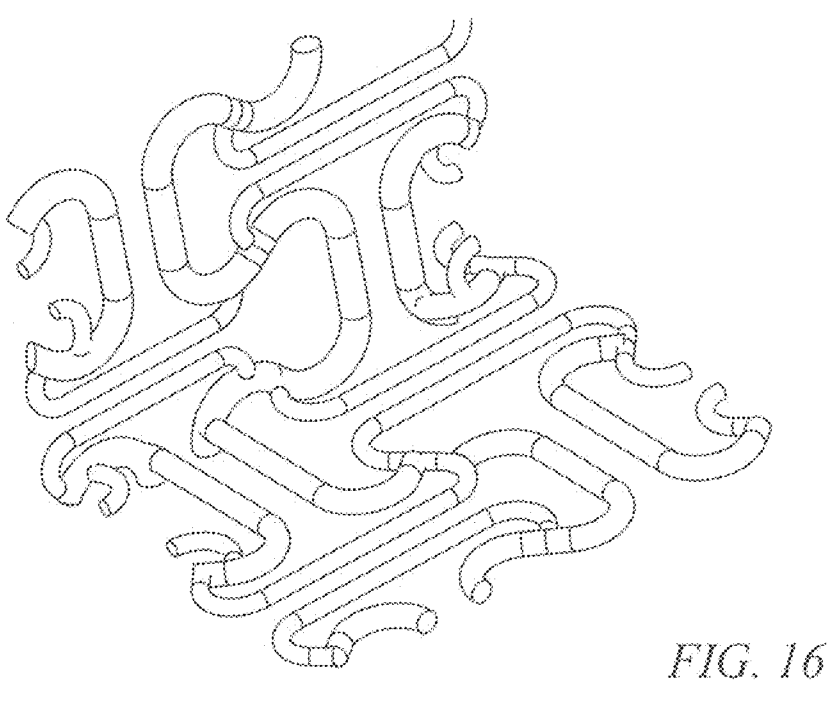
FIG. 16 illustrates a 3-D representation of an exemplary embodiment of the porous structure of the present invention comprising one or more frame configurations in FIGS. 13A-13M, including frames for struts that are straight, curved, or a combination of both.

Referring to FIGS. 13A-13M, the present invention also provides for embodiments that reduce the effect of stress risers by incorporating curved struts into the porous structures. FIGS. 13A-13M illustrate 2-D representations of these various exemplary configurations of the frame of the two struts of the present invention forming a node, including frames for struts that are straight, curved, or a combination of both. As shown, only two struts intersect each other at the node 1302. At least in FIGS. 13A-13C, the struts intersect one another tangentially at the node 1302, providing increased mechanical strength and bonding. FIG. 14 illustrates 2-D representation of an exemplary embodiment of the porous structure of the present invention comprising one or more frame configurations in FIGS. 13A-13M, including frames for struts that are straight, curved, or a combination of both. As shown by FIG. 14, no more than two struts, whether curved or straight, meet at each node. FIGS. 15A-15C illustrate 2-D representations of exemplary configurations of the present invention of various curved frames and corresponding struts intersecting to form a node 1502. In FIGS. 15A-15C, the dashed lines represent the frames 1504 and the solid lines represent the corresponding struts 1506. As shown, node 1502*a* is formed where the circular strut with its center at 1508 tangentially intersect or meet the circular strut with its center at 1510. The node 1502*b* is formed where the circular strut with its center at 1508 tangentially intersect or meet the circular strut with its center at 1512. Similarly, FIG. 15B shows the circular strut with its center at 1514 tangentially intersecting the circular strut with its center at 1516 to form node 1502*c*. Likewise, FIG. 15C shows the circular strut with its center at 1518 tangentially intersecting the circular strut with its center at 1520 to form node 1502*d*. FIG. 16 illustrates a 3-D representation of an exemplary embodiment of the porous structure of the present invention comprising one or more frame configurations in FIGS. 13A-13M, including frames for struts that are straight, curved, or a combination of both.

Figure 17:
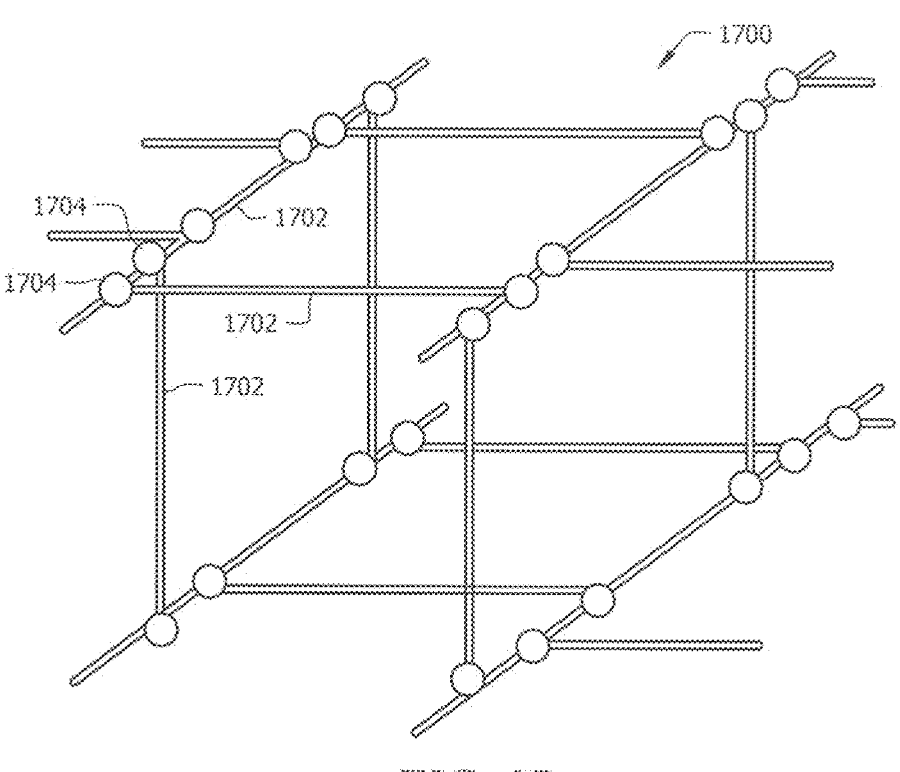
FIG. 17 illustrates a 3-D representation of an exemplary frame for a generally cubical cell of the porous structure of the present invention.
Figure 18:
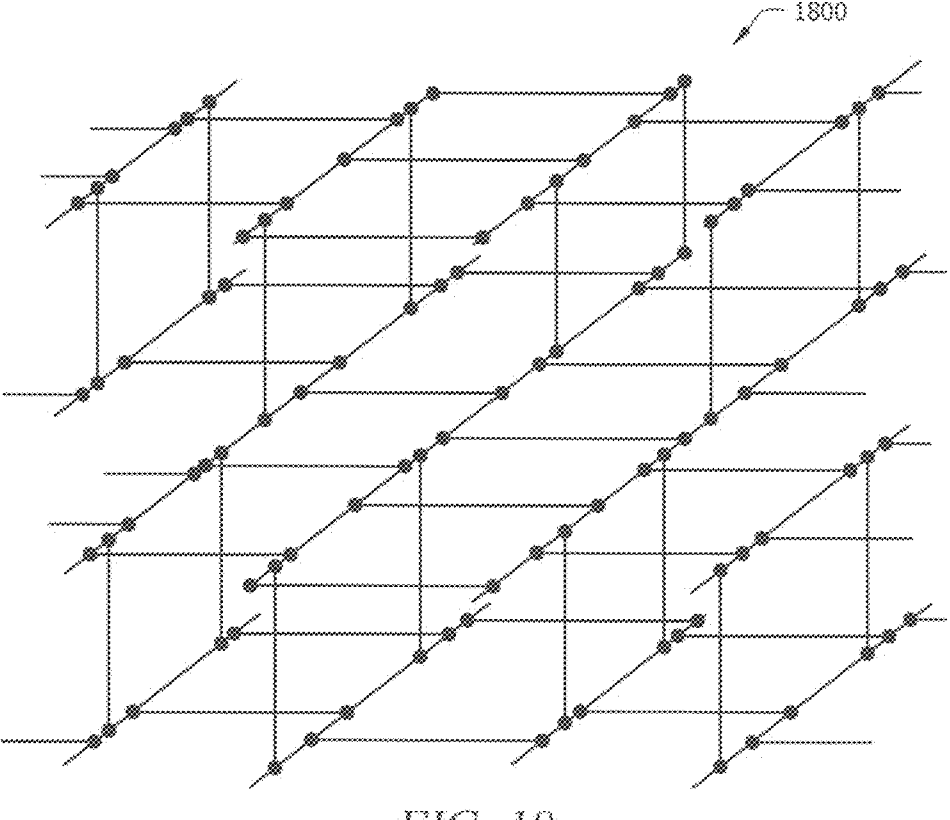
FIG. 18 illustrates a 3-D representation of an exemplary arrangement of frames for cubical cells in FIG. 17.
Figure 19:
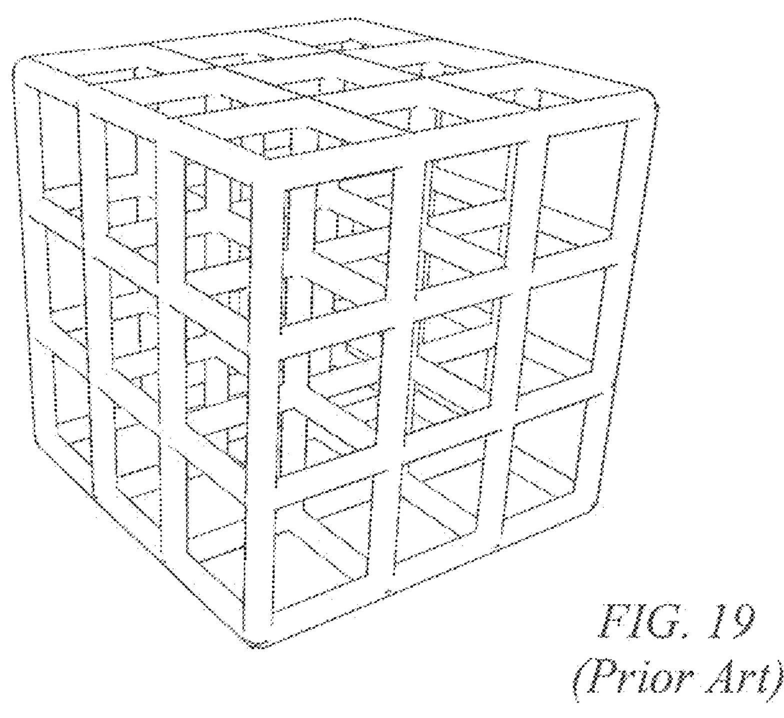
FIG. 19 illustrates a 3-D representation of an arrangement of cubical cells of the porous structure of the prior art.
Figure 20:
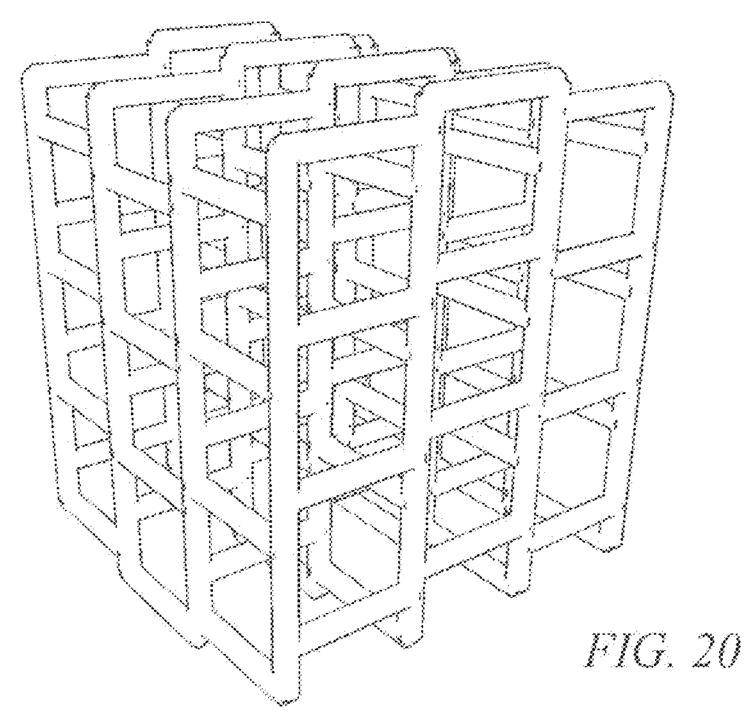
FIG. 20 illustrates a 3-D representation of an exemplary arrangement of cubical cells of the porous structure of the present invention.
Figure 21:
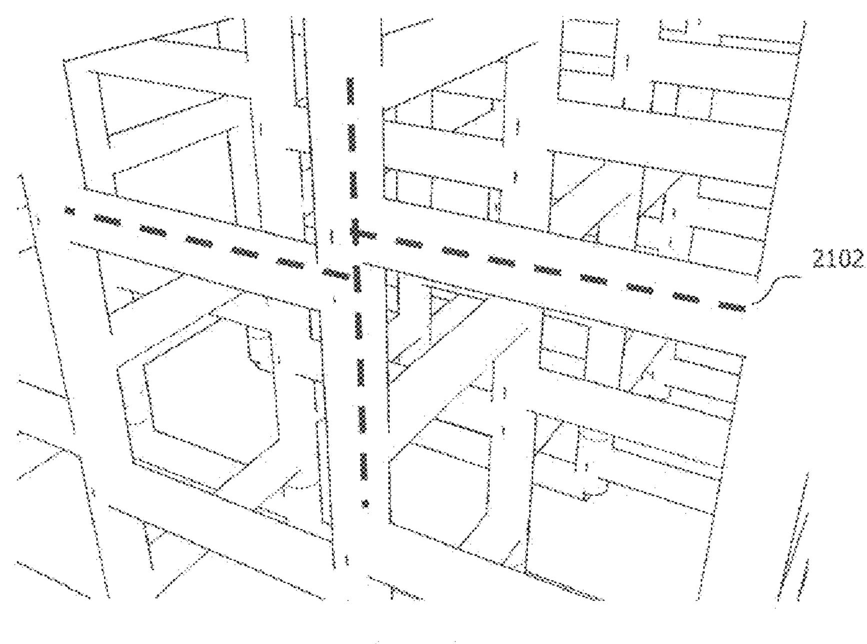
FIG. 21 illustrates a blown up view of the arrangement in FIG. 20.

FIG. 17 illustrates a 3-D representation of an exemplary frame for a generally cubical cell 1700 formed by twelve struts 1702 and sixteen nodes 1704. Again, for simplification purposes, only some of the struts and nodes are labeled. By using sixteen nodes 1704 that form connections between only two struts 1702 as opposed to eight nodes that form connections between three struts as in a conventional cube design (not shown), the cell 1700 provides stronger nodes 1704, and stronger connections between the struts 1702 and nodes 1704. As a result, this novel configuration of one embodiment of the present invention avoids variations in cross-sectional diameters between struts 1702 and nodes 1704. As a result, the negative effects of stress risers like those shown at stress risers 106 and 114 in FIGS. 1A-1B on the strength of the structure are lessened. FIG. 18 illustrates a porous structure 1800 formed from a plurality of connected cells 1802, which are similar to those shown in FIG. 17. Similarly, FIGS. 19-20 show another comparison between the arrangement of cells of the prior art in FIG. 19 and one embodiment the arrangement of cells of the present invention in FIG. 20. As previously discussed, by having more than two struts intersect at a node, the porous structure of the prior art is weak due to the increased effect of the stress risers. On the other hand, the arrangement in FIG. 20 of the present invention provides the requisite porosity with an improved strength because no more than two struts intersect at a node. In addition, the arrangement of FIG. 20 has the added benefit of having more trabecular features, resembling the characteristics of cancellous bone, unlike the regular prior art configuration. Moreover, the advantage of looking trabecular while being formed in a calculated manner provides another benefit to the porous structures formed in accordance with the invention a decreased need for expansive randomization of the porous structure. Consequently, the arrangement of FIG. 20 resembles the characteristics of bones more so than the prior art configuration of FIG. 19. FIG. 21 is a blown up view of the arrangement in FIG. 20 where the dashed lines 3102 represent the frames of the struts to better show where the struts meet to form a node.

Figure 22:
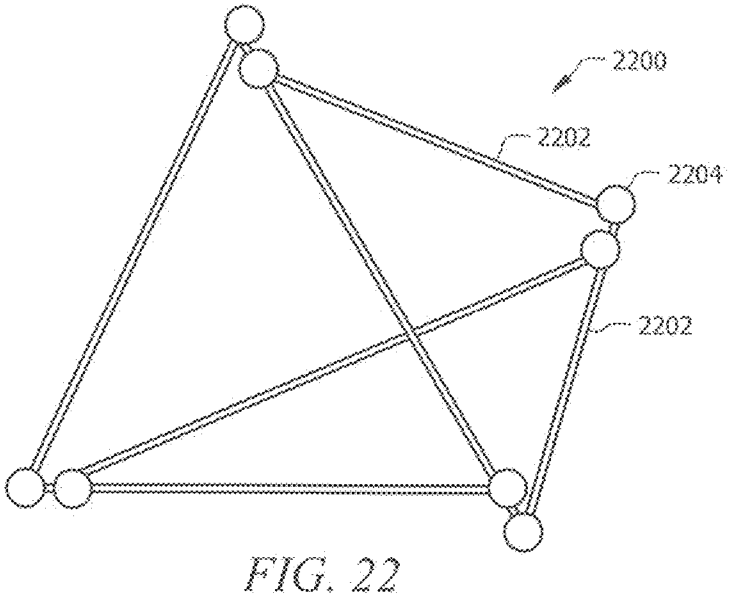
FIG. 22 illustrates a 3-D representation of an exemplary frame for a tetrahedron-shaped cell of the porous structure of the present invention.
Figure 23:
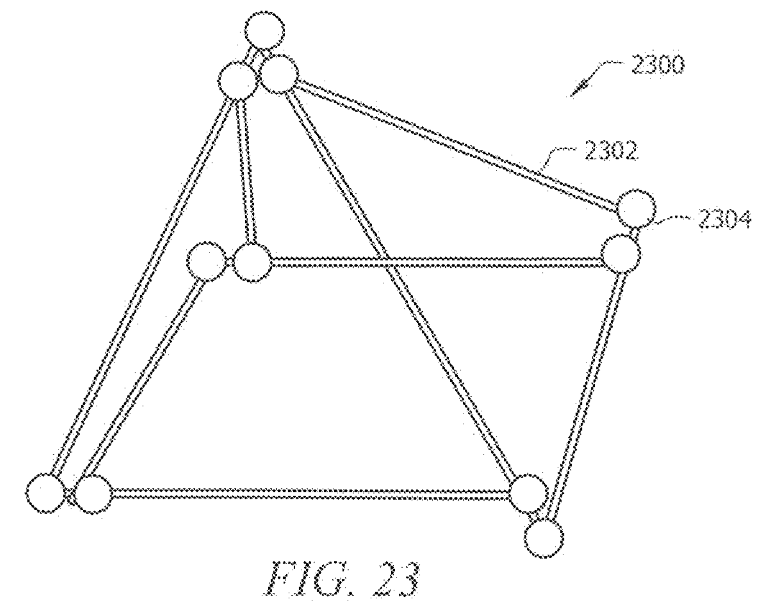
FIG. 23 illustrates a 3-D representation of an exemplary frame for square-based pyramid cell of the porous structure of the present invention.

Similarly, FIG. 22 illustrates another embodiment of a cell of the present invention. Cell 2200 is based on a tetrahedron-shaped cell, or a triangular pyramid, where it is formed using only six struts 2202 and eight nodes 2204. Each node 2204 connects only two struts 2202 together. FIG. 23 illustrates a similar cell 2300, which is a square-based pyramid. Referring to FIG. 23, eight struts 2302 and eleven nodes 2304 are used to form the cell 2300. Other geometrical shapes for cells, such as dodecahedrons, icosahedrons, octagonal prisms, pentagonal prisms, cuboids, and various random patterns are discussed below. In addition, FIGS. 17, 18, 22 and 23 illustrate frames of struts that can be built from these frames where the thickness of each strut can be selected. As such, the thickness for each strut can be uniform or vary from one strut to another strut. Further, the struts can incorporate the fluted starts of FIGS. 6-8. In addition, the struts do not have to be cylindrical in shape. As further discussed below, the cross-section of the struts can be rectangular or square or any other shape, e.g., geometric shape or irregular shapes, that would be suitable for the application.

As discussed above with respect to FIGS. 17, 18, 22, and 23, various cell designs of various shapes can be created using various techniques discussed above, e.g., DMF. Generally speaking, almost any three-dimensional multiple-sided design may be employed. For example, cells with an overall geometric shape such as Archimedean shapes, Platonic shapes, strictly convex polyhedrons, prisms, anti-prisms, and various combinations thereof are within the contemplation of the present invention. In other embodiments, the number of sides of each cell may range from about 4 to about 24. More preferably, the number of sides-of each cell may range from about 4 to about 16. One geometry that has been found to be particularly effective is a dodecahedron or 12 sided cell. However, as explained and illustrated below, the geometries of the individual cells or the cells of the porous structure may vary widely and, in the geometries, may vary randomly from cell to cell of a porous structure.

For example, FIGS. 24A and 24B illustrate a conventionally designed dodecahedral cell 2400 from a prior art porous structure with each node 2404 being a connection between, three struts 2402. Again, U.S. Publication. Nos. 2006/0147332 and 2010/0010638 disclose examples of porous structures formed from these conventional cells. A porous structure with a given porosity and having a desired volume can be formed using a plurality of cells 2400 by attaching one cell 2400 to another cell 2400 until the desired volume is achieved. Further, the structures using the prior art cell configuration, may be disadvantageous because they do not resemble the randomness of native cancellous structures. That is, they do not adequately resemble the features of trabecular bone. More importantly, referring to FIGS. 24A and 24B, higher stresses are placed at each node 2404 because the struts 2402 intersect one another at 120. degree. angles, thereby increasing stress concentration factors due to the formation of notches or grooves on the face of the nodes 2404 and the connection between more than two struts 2402 at each node 2404.

FIGS. 25A and 25B illustrate one embodiment of the present invention that provides a solution to these problems of the prior art. As shown by FIGS. 25A and 25B, cell 2500 eliminated the conventional nodes 2404 in FIGS. 24A and 24B by using curved struts 2502 that form a ring or hoop, thereby eliminating the stress concentration factors caused by these nodes. In addition, cells 2500 replace conventional nodes 2404 in FIGS. 24A and 24B with modified nodes 2504 that can be open or porous to provide additional porosity, which is an added benefit for many applications, such as enhancing tissue/bone ingrowth for orthopedic implants. Accordingly, cell 2500 provides additional strength with increased porosity while the conventional cell 2400 is weaker and less porous.

Figure 26:
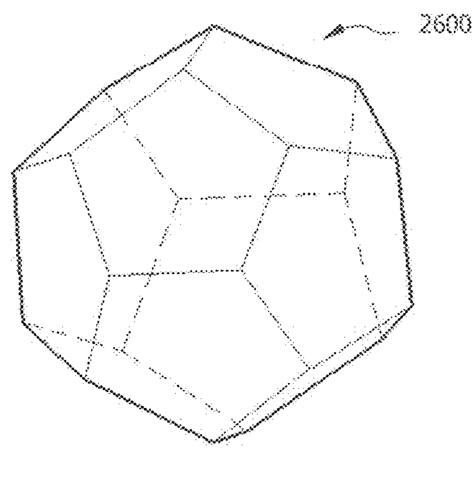
FIGS. 26-28 illustrate 3-D representations of a frame of the convention cell in FIGS. 24A and 24B modified by one embodiment of the present invention.
Figure 27:
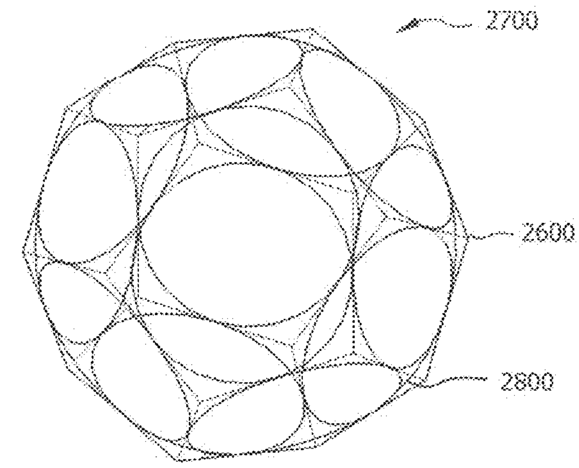
Figure 28:
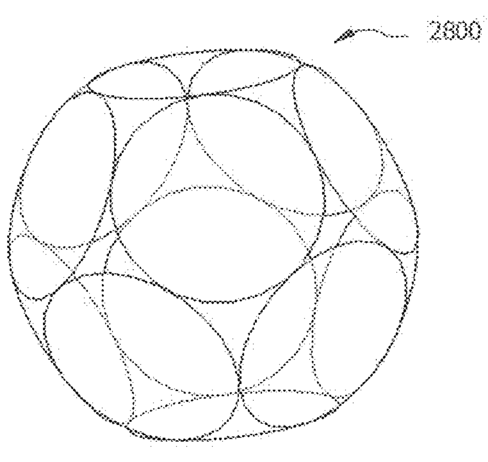
Figure 29A:
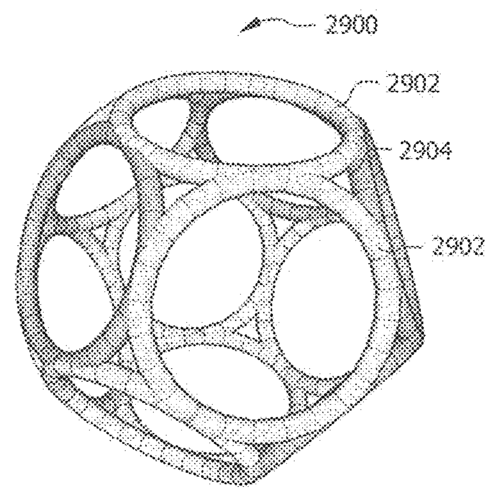
FIGS. 29A and 29B illustrate 3-D representations of a cell of the present invention formed from FIGS. 26-28, where
Figure 29B:
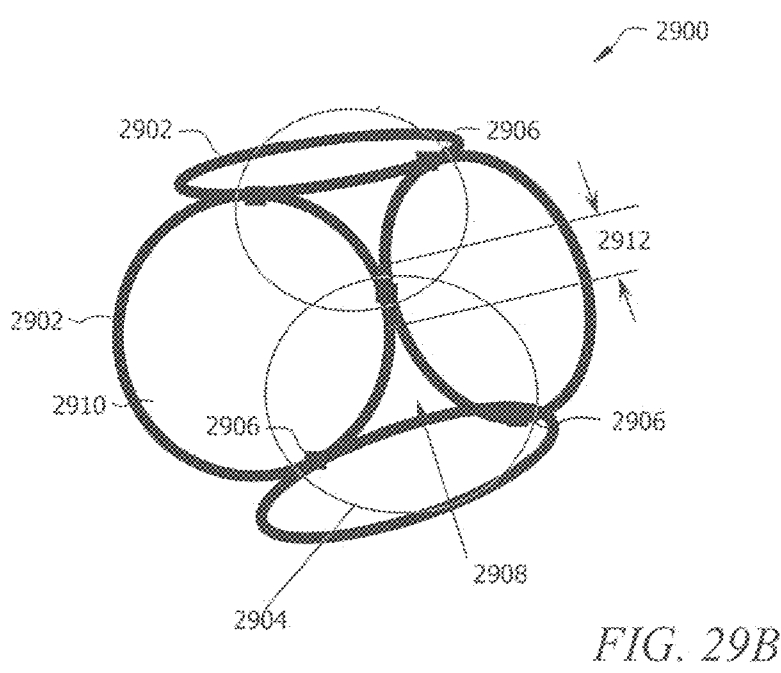

FIGS. 26-28 illustrate one embodiment to forming the cell in FIGS. 25A and 25B. FIG. 26 illustrates a dodecahedral frame 2600 for prior art cells as discussed with respect to FIGS. 24A and 248. FIG. 27 illustrates frame 2700 which comprises frame 2800 of FIG. 28 superimposed over the dodecahedral frame 2600 of FIG. 26. FIG. 29A illustrates a cell similar to that of FIGS. 25A and 25B formed by selecting a thickness for frame 2800. In FIG. 29A, the cell 2900 is constructed from twelve curved struts 2902 that, in this embodiment, may form a ring, a loop, an annulus, or a hoop. The curved struts 2902 are joined together at triangular modified nodes 2904 that are more easily seen in FIGS. 29B. Referring to FIG. 29B, the thicker circles represent four of the curved struts 2902 of the cell 2900 while the thinner circles highlight the modified nodes 2904 formed by struts 2902. Each modified node 2904 includes three fused connections or sintering junctions 2906 between two different curved struts 2902. That is, curved struts 2902 tangentially intersect one another at the respective junction 2906. Depending on the thickness of each strut 2902, modified node 2904 may also be porous with openings 2908 disposed between the three junctions 2906 or occluded with no openings disposed between the three junctions 2906. Preferably, modified node 2904 has openings 2908 disposed between the three junctions 2906 to provide additional porosity in conjunction with the porosity provided by the fenestrations 2910 of the curved struts 2902. Referring to FIG. 29B, while the struts 2906 tangentially intersect one another, e.g., their frame tangentially meet, the struts' thickness may render the individual junctions 2906 relatively long as indicated by the distance 2912. These long, generally tangential sintering junctions 2906 provide increased mechanical strength and bonding.

Figure 30:
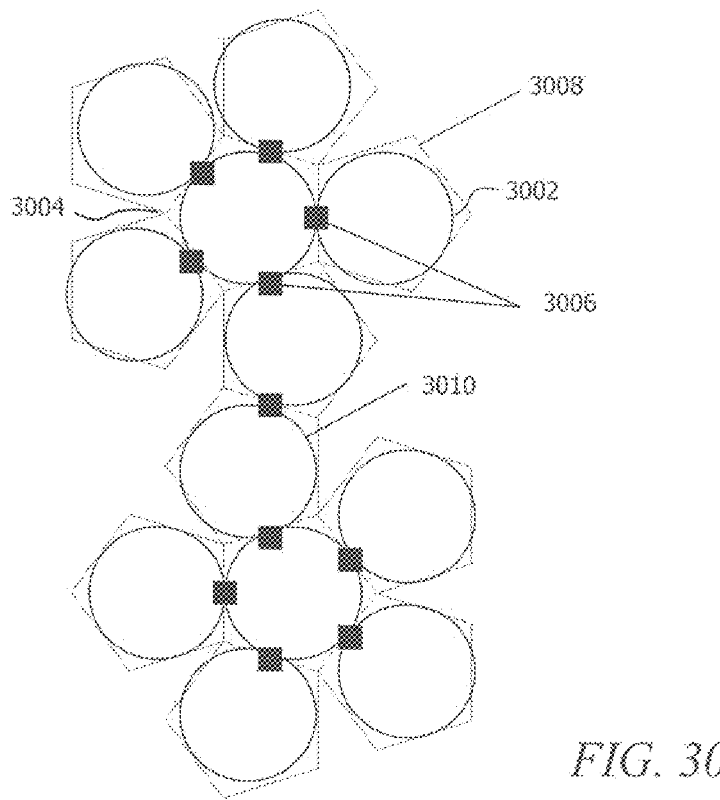
FIG. 30 illustrates the frame of FIG. 27 unfolded into a 2-D representation.

Referring to FIG. 30. it depicts an unfolded or flattened two-dimensional representation of FIG. 27, with conventional frame 3008 and the frame 3010 of cell 2900. As shown by FIG. 30, the location and number of individual junctions 3006, as compared to conventional nodes 3004 of the conventional configuration 3008, is different when using curved struts 3002 provided by the invention. For example, junctions 3006 are generally located around the center of the body of curved struts 3002, while conventional nodes 3002 is located at the end of the conventional struts. In addition, in this particular embodiment, the number of junctions 3006 where the curved struts 3002 meet is three times the number of conventional nodes 3004 where straight struts meet for frame 3008. Accordingly, the increased number of junctions provide increased mechanical strength.

Figure 31:
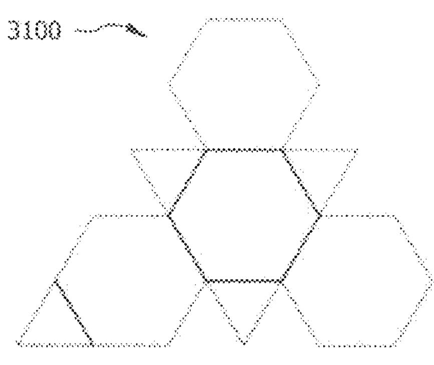
FIG. 31 illustrates a frame of a truncated tetrahedral cell unfolded into a 2-D representation.
Figure 32:
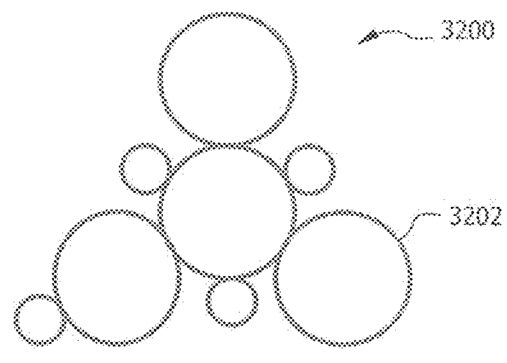
FIG. 32 illustrates the frame of FIG. 31 formed with curved struts according to one embodiment of the present invention.
Figure 33:
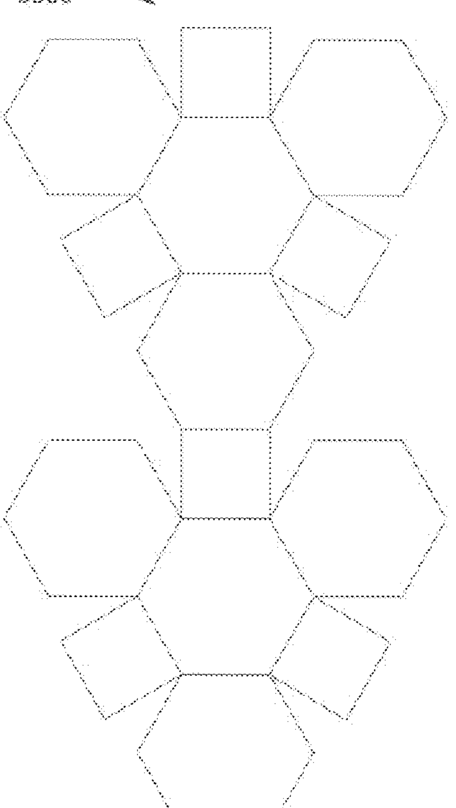
FIG. 33 illustrates the frame of a truncated octahedral cell unfolded into a 2-D representation.
Figure 34:
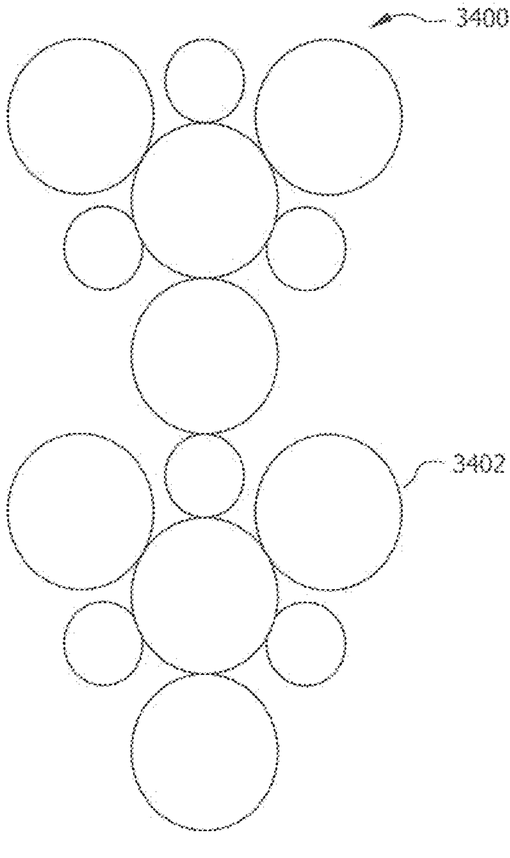
FIG. 34 illustrates the frame of FIG. 33 formed with curved struts according to one embodiment of the present invention.

FIGS. 31-34 illustrate how frames for cells based on a typical polyhedron can be modified with curved struts to form a cell similar to cell 2900 of FIG. 29. Specifically, FIG. 31 illustrates a frame 3100 of a truncated tetrahedral cell unfolded into a 2-D representation. In FIG. 32, frame 3202 represents frame 3100 of FIG. 31 as modified by one embodiment the present invention to be formed with curved struts 3202. Similarly, FIG. 33 Illustrates the frame 3300 of a truncated octahedral cell unfolded into a 2-D representation, and frame 3402 of FIG. 34 represents frame 3300 of FIG. 31 as modified by one embodiment the present invention to be formed with curved struts 3402. As discussed above, e.g., with respect to FIG. 30, the cells formed with frames 3200 and 3400 have increased mechanical strength and porosity over frames 3100 and 3300, respectively.

Figures 35A, 35B, 35C:
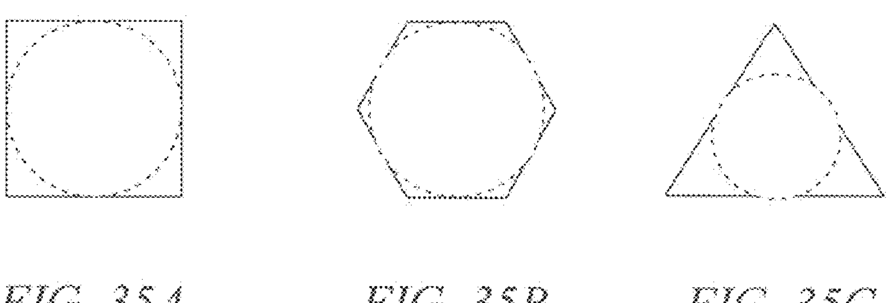
FIGS. 35A-35E illustrate 2-D representations of examples of a circle or an ellipse inscribed within various geometric shapes according to one embodiment of the present invention.
Figures 35D, 35E:
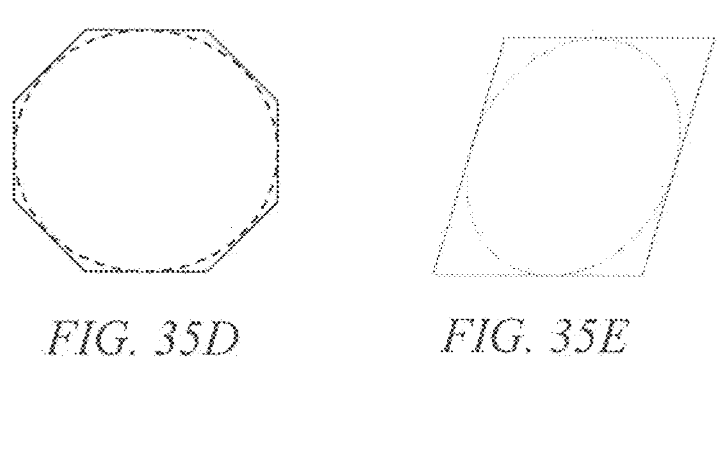

FIGS. 35A-35B illustrate one way of modifying a typical polyhedron frame with curved struts. According to one embodiment of the invention, the polyhedron can be modified by inscribing, within the polyhedron, a circle or other shapes that contain curved features, such as an ellipse or oblong. Specifically, FIG. 35A is a circle inscribed within a square, FIG. 35B is a circle inscribed within a hexagon, FIG. 35C is a circle inscribed within a triangle, FIG. 35D is a circle inscribed within an octagon, and FIG. 35E is an oval inscribed within a parallelogram. FIGS. 35A-35B are merely demonstrative of the different configurations available and are not intended to limit the scope of the invention.

Figure 36:
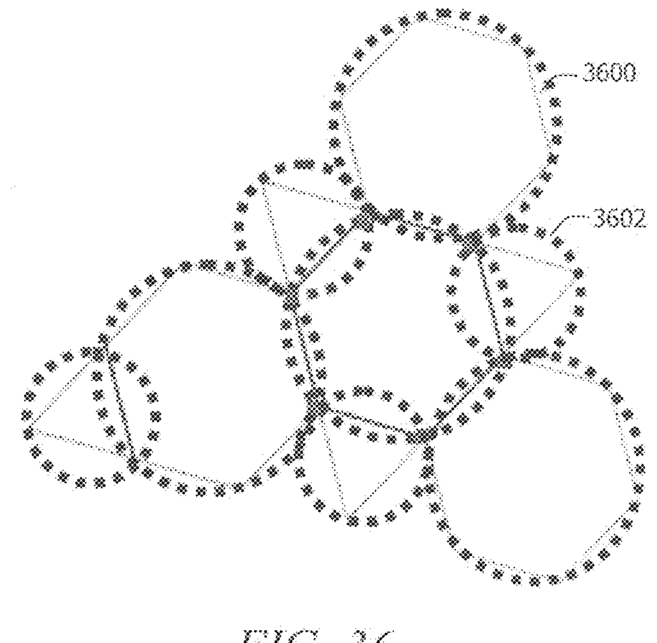
FIG. 36 illustrates the frame of a truncated tetrahedral cell unfolded into a 2-D representation with circles circumscribed around each face of the cell according to one embodiment of the present invention.

FIG. 36 illustrates another way of modifying a typical polyhedron frame with curved struts. According to another embodiment of the invention, the polyhedron can be modified by circumscribing the polyhedron with a circle or other shape that contain curved features, such as an ellipse or oblong. FIG. 36 illustrates a frame 3600 of a truncated tetrahedral cell with circles 3602 circumscribed around each face of the cell. Some or all portions of frame 3600 may be removed to form a new cell frame that can be used to fabricate a porous structure according to the present invention.

FIGS. 37-39 illustrate embodiments of the present invention that incorporate both straight and curved struts. Specifically, FIGS. 37A and 37B illustrate cell 3700 formed from frame 2700 of FIG. 27, which is a combination of the dodecahedral frame 2600 of FIG. 26 with frame 2800 of FIG. 28. Cell 3700 has increased strength due to the addition of the curved struts, which result in a blending of the stress risers. As shown, cell 3700 has modified node 3704 comprising a conventional node formed with straight struts 3702*b* and a node formed by three junctions of the curved struts 3702*a*. FIG. 38 illustrates cell 3800 formed by keeping one or more conventional nodes 3804 formed by straight struts 3802 while modifying the other struts of the cells with curved struts 3806 to form junctions 3808 and modified nodes 3810. In FIG. 38 some struts ate selectively thicker than other struts, depending on applications.

Referring to FIG. 38, the cell 3800 has at least one curved strut 3802, and preferably a plurality of curved struts 3802 that form modified node 3804*a* when joined with two other curved struts 3802. In other embodiments, the modified nodes can be formed by joining together curved struts, curbed strut sections, straight struts, or straight sections, or combinations thereof. An example of a node formed by joining together straight and curved struts is shown in FIGS. 39A-39C as modified node 3904*b*. Modified nodes 3804*a* are preferably triangular formed by three junctions 3806. Cell 3800 may contain some convention nodes 3808 that join straight struts 3810 or straight strut sections that may comprise notches formed by intersecting angles practiced in the prior art. The modified node 3804*a* may be porous as discussed previously and indicated by 3804*a* or occluded as indicated at 3804*b*. The occluded modified nodes 3804*b* and the porous modified nodes 3804*a* may be formed by tangent sintering three or more junctions 3806 between curved or "ring-like" 0 struts together. Any combination of occluded nodes 3804*b*, porous modified nodes 3804*a*, conventional nodes 3808, straight struts 3810, curved struts 3802, and portions or segments thereof may be used in different predetermined or random ways in order to create stronger, more cancellous-appearing cell structure. Referring to FIGS. 39A-39C, cell. 3900 is an example of such combination. Cell 3900 has curved struts 3902*a* that are "ring-like" and struts 3902*b*. It also has straight struts 3906 and conventional nodes 3908. The combination of struts forms porous modified nodes 3904*a* and occluded modified nodes 3904*b*.

Thus, while the cells 3800 within a porous structure may be homogeneous, they may be arranged in a random and/or predetermined fashion with respect to each other to more closely resemble the appearance of cancellous bone. In some instances, it may be desirable to utilize one or more heterogeneous cell configurations which may be arranged systematically in predetermined patterns and/or arranged in random fashion to create a porous structure. Various arrangements can be designed using computer aided design (CAD) software or other equivalent software as will be apparent to those skilled in the art.

Figure 41B:
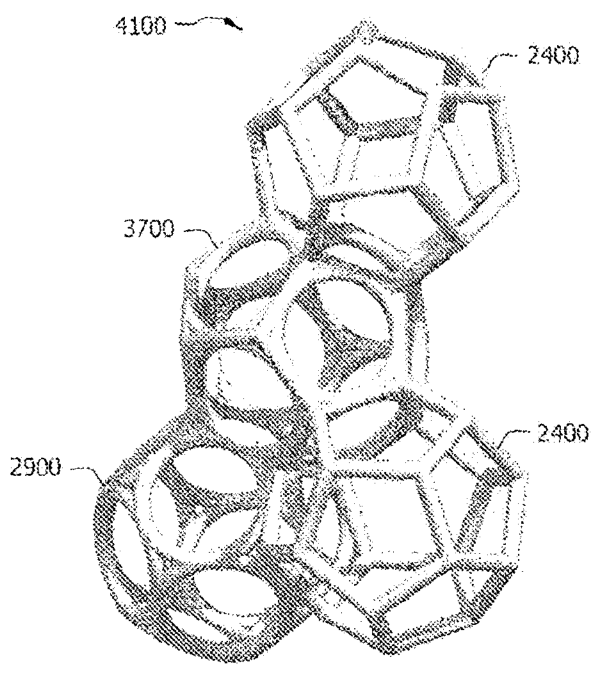

FIGS. 40 and 41 show exemplary configurations of how the cells 2400, 2900, and 3700 from FIGS. 24, 29, and 37, respectively, can be combined, e.g., attached, joined, tiled, stacked, or repeated. Specifically, FIG. 40 illustrates arrangement 4000 comprising cell 2400 and cell 2900 from FIGS. 24 and 29, respectively. In arrangement 4000, at the face where cell 2400 attaches to cell 2900, conventional nodes 2404 is placed partially within modified nodes 2904. Accordingly, by using various combinations of cells 2400 and cells 2900, or other cells formed according to the present invention, a number of modified nodes 2504 can be selectively occluded completely or partially by matching conventional nodes with modified nodes. FIGS. 41A and 41B illustrate arrangement 4100 comprising cells 2400, 2900, and 3700. Again, FIGS. 40 and 41 are illustrative and do not limit the combination that can be made with these cells or other cells formed according to the embodiments of the present invention.

Figure 42:
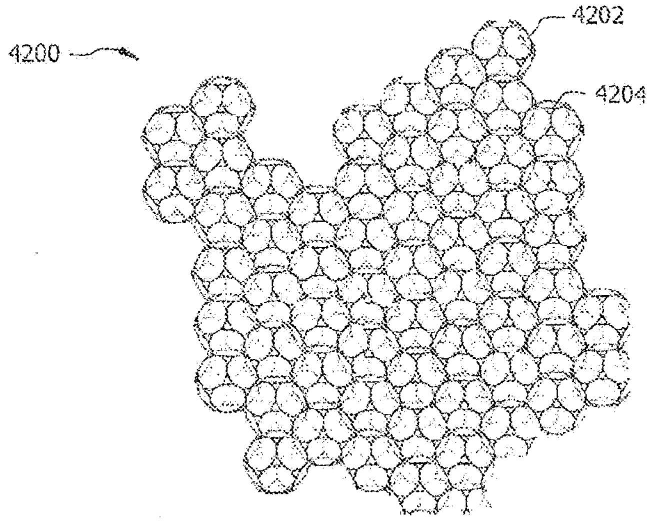
FIG. 42 illustrates a 3-D representation of an exemplary arrangement of the cells based on a truncated tetrahedral shape having one or more curved struts.

FIG. 42 illustrates a porous structure 5300 formed by joining a plurality of cells 4202 together, where the shape of cells 4202 is based on a truncated tetrahedron. One or more curved struts 4204 which may or may not form complete rings are inscribed within, or circumscribed around, each face of the selected polyhedral shape, which is a truncated tetrahedron in FIG. 42. Alternatively, the truncated tetrahedron shape or other selected polyhedral shape may be formed using a large number of short straight struts to closely approximate truly curved ring struts, such as the ring struts of cell 2900 in FIG. 29.

FIGS. 43-45 illustrate 3-D representations of exemplary arrangements cells formed in accordance with the embodiments of the present invention. Specifically, FIG. 43 illustrates one way cells based on truncated octahedra can be stacked to form bitruncated cubic honeycomb structure 4300, which is by space-filling tessellation. The cells of structure 4300 in both shades of gray are truncated octahedra. For simplification purposes, each cell is not modified with a curved strut but rather the dashed circle serves to illustrate that one or more faces or one or more truncated octahedra can be modified according to the embodiments of the present invention, e.g., curved struts to form porous structures with increased strength and porosity. Similarly, FIG. 44 illustrates one way, e.g., space-filling tessellation, cells based on a combination of cubes (light grey), truncated cuboctahedra (black), and truncated octahedra (dark grey) can be stacked to form cantitruncated cubic honeycomb structure 4400. Again, it is understood that the dashed circles represent how one or more polyhedron of porous structure 4400 can be modified according to the embodiments of the present invention, e.g., curved struts to form porous structures with increased strength and porosity. Likewise, FIG. 45 illustrates one way, e.g., space-filling tessellation, cells based on a combination of cuboctahedra (black), truncated octahedra (dark grey) and truncated tetrahedra (light grey) can be stacked to form truncated alternated cubic honeycomb structure 4500. Again, it is understood that the dashed circles represent how one or more polyhedron of structure 4500 can be modified according to the embodiments of the present invention, e.g., curved struts to form porous structures with increased strength and porosity.

Figure 46:
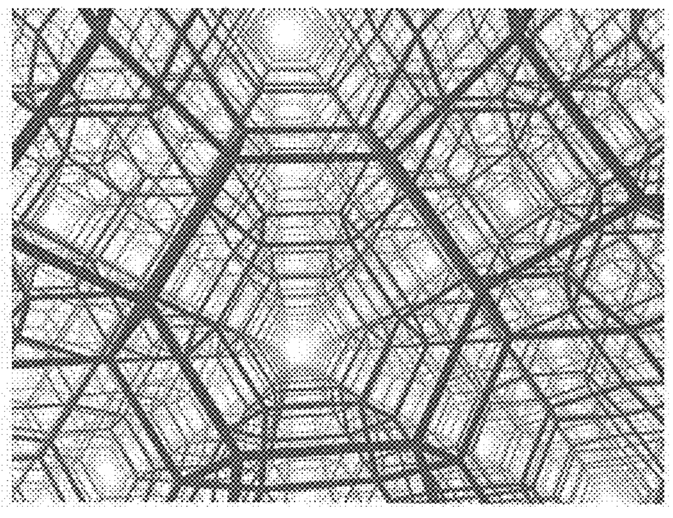
FIG. 46 illustrates a flame view of the arrangement of FIG. 42.
Figure 47:
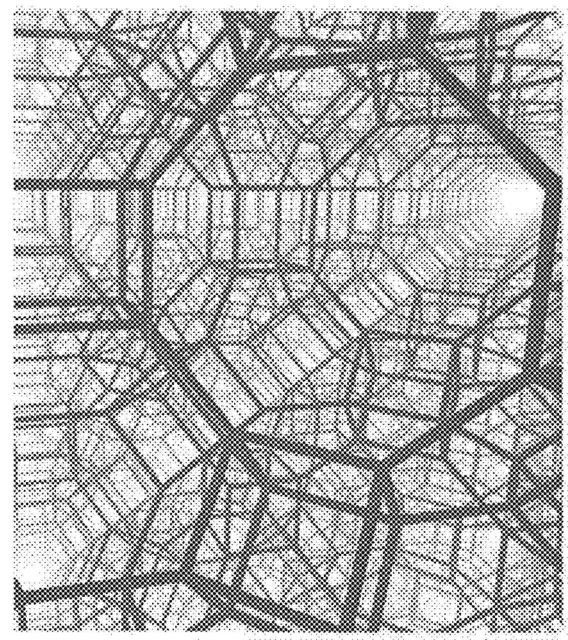
FIG. 47 illustrates a frame view of the arrangement of FIG. 43.
Figure 54D:
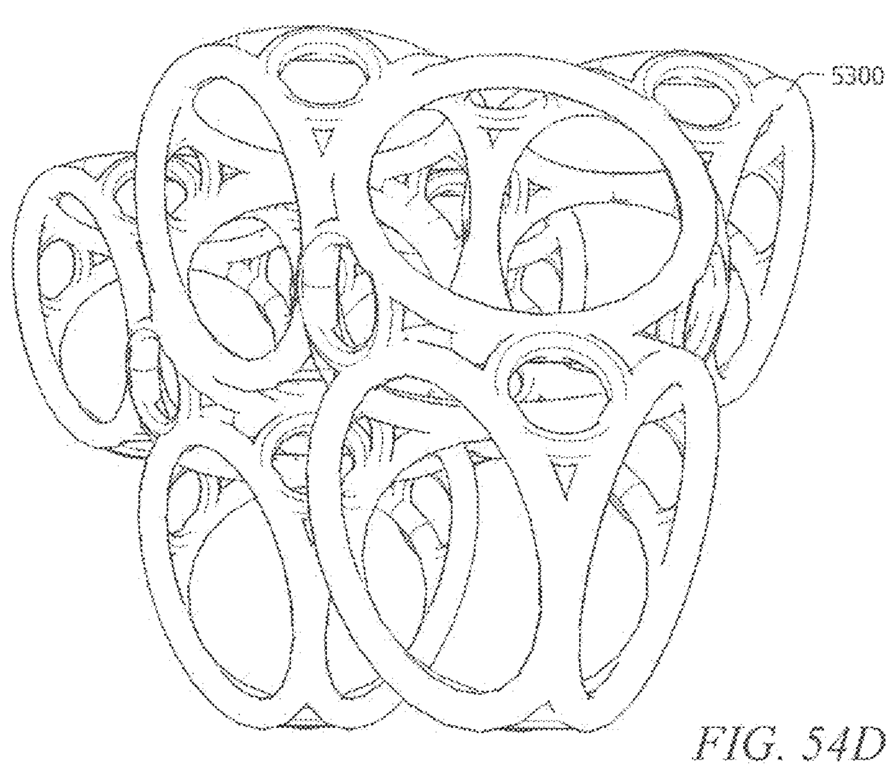
Figure 54E:
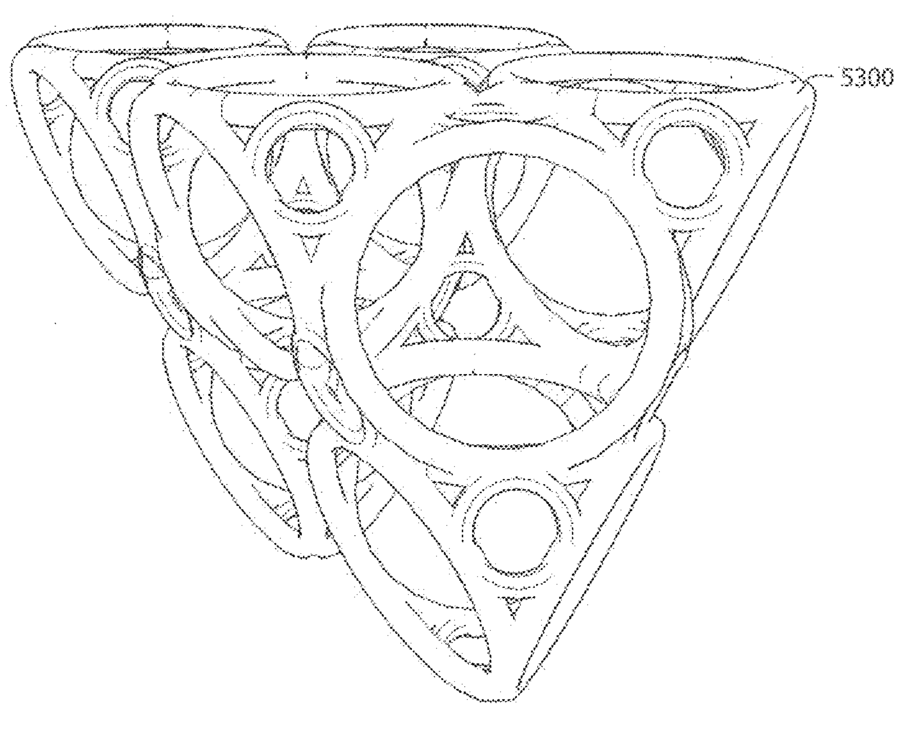

FIG. 46 illustrates a frame view of the bitruncated cubic honeycomb structure 4300 of FIG. 43. FIG. 47 illustrates a frame view cantitruncated cubic honeycomb structure 4500 of FIG. 45. As shown by FIGS. 46 and 47, porous structures formed with polyhedral are not random, and thus, are not as suitable for implantation purposes, particularly for bones, because they do not adequately resemble the features of trabecular bone. On the other hand, as it can be envisioned that modifying certain or all cells of the frames in FIGS. 46 and 47 would result in porous structures resembling trabecular bone.

When curved struts are employed, at least one curved strut portion may generally form a portion of a ring which at least partially inscribes or circumscribes a side of a polyhedron. Such a polyhedral shape may be any one of isogonal or vertex-transitive, isotoxal or edge-transitive, isohedral or face-transitive, regular, quasi-regular, semi-regular, uniform, or noble. Disclosed curved strut portions may also be at least partially inscribed within or circumscribed around one or more sides of one or more of the following Archimedean shapes; truncated tetrahedrons, cuboctahedrons, truncated cubes (i.e., truncated hexahedrons), truncated octahedrons, rhombicuboctahedrons (i.e., small rhombicuboctahedrons), truncated cuboctahedrons (i.e., great rhombicuboctahedrons), snub cubes (i.e., snub hexahedrons, snub cuboctahedrons—either or both chiral forms), icosidodecahedrons, truncated dodecahedrons, truncated isosahedrons (i.e., buckyball or soccer ball-shaped), rhombicosidodecahedrons (i.e., small rhombicosidodecahedrons), truncated icosidodecahedrons (i.e., great rhombicosidodecahedrons), snub dodecahedron or snub icosidodecahedrons (either or both chiral forms). Since Archimedean shapes are highly symmetric, semi-regular convex polyhedrons composed of two or more types of regular polygons meeting in identical vertices, they may generally be categorized as being easily stackable and arrangeable for use in repeating patterns to fill up a volumetric space.

In some embodiments, curved strut portions according to the invention are provided to form a porous structure, the curved strut portions generally forming a ring strut portion at least partially inscribing within or circumscribing around one or more polygonal sides of one or more Platonic shapes (e.g., tetrahedrons, cubes, octahedrons, dodecahedrons, and icosahedrons), uniform polyhedrons (e.g., prisms, prismatoids such as antiprisms, uniform prisms, right prisms, parallelepipeds, and cuboids), polytopes, polygons, polyhedrons, polyforms, and/or honeycombs. Examples of antiprisms include, but are not limited to square antiprisms, octagonal antiprisms, pentagonal antiprisms, decagonal antiprisms, hexagonal antiprisms, and dodecagonal antiprisms.

In yet other embodiments, a porous structure may be formed from cells comprising the shape of a strictly convex polyhedron, (e.g., a Johnson shape), wherein curved strut portions generally form a ring strut portion at least partially inscribed within or circumscribed around one or more face of the strictly convex polyhedron, wherein each face of the strictly convex polyhedron is a regular polygon, and wherein the strictly convex polyhedron is not uniform (i.e., it is not a Platonic shape, Archimedean, shape, prism, or antiprism). In such embodiments, there is no requirement that each face of the strictly convex polyhedron must be the same polygon, or that the same polygons join around each vertex. In some examples, pyramids, cupolas, and rotunda such as square pyramids, pentagonal pyramids, triangular cupolas, square cupolas, pentagonal cupolas, and pentagonal rotunda, are contemplated. Moreover, modified pyramids and dipyramids such as elongated triangular pyramids (or elongated tetrahedrons), elongated square, pyramids (or augmented cubes), elongated pentagonal pyramids, gyroelongated square pyramids, gyroelongated pentagonal pyramids (or diminished icosahedrons), triangular dipyramids, pentagonal dipyramids, elongated triangular dipyramids, elongated square dipyramids (or biaugmented cubes), elongated pentagonal dipyramids, gyroelongated square dipyramids may be employed. Modified cupolas and rotunda shapes such as elongated triangular cupolas, elongated square cupolas (diminished rhombicuboctahedrons), elongated pentagonal cupolas, elongated pentagonal rotunda, gyroelongated triangular cupolas, gyroelongated square cupolas, gyroelongated pentagonal cupolas, gyroelongated pentagonal rotunda, gyrobifastigium, triangular orthobicupolas (gyrate cuboctahedrons), square orthobicupolas, square gyrobicupolas, pentagonal orthobicupolas, pentagonal gyrobicupolas, pentagonal orthocupolarotunda, pentagonal gyrocupolarotunda, pentagonal orthobirotunda (gyrate icosidodecahedron), elongated triangular orthobicupolas, elongated triangular gyrobicupolas, elongated square gyrobicupolas (gyrate rhombicuboctahedrons), elongated pentagonal orthobicupolas, elongated pentagonal gyrobicupolas, elongated pentagonal orthocupolarotunda, elongated pentagonal gyrocupolarotunda, elongated pentagonal orthobirotunda, elongated pentagonal gyrobirotunda, gyroelongated triangular bicupolas (either or both chiral forms), gyroelongated square bicupolas (either or both chiral forms), gyroelongated pentagonal bicupolas (either or both chiral forms), gyroelongated pentagonal cupolarotunda (either or both chiral forms), and gyroelongated pentagonal birotunda (either or both chiral forms) may be utilized. Augmented prisms such as augmented triangular prisms, biaugmented triangular prisms, triaugmented triangular prisms, augmented pentagonal prisms, biaugmented pentagonal prisms, augmented hexagonal prisms, parabiaugmented hexagonal prisms, metabiaugmented hexagonal prisms, and triaugmented hexagonal prisms may also be practiced with the invention. Modified Platonic shapes such as augmented dodecahedrons, parabiaugmented dodecahedrons, metabiaugmented dodecahedrons, triaugmented dodecahedrons, metabidiminished icosahedrons, tridiminished icosahedrons, and augmented, tridiminished icosahedrons may be employed. Moreover, modified Archimedean shapes such as augmented truncated tetrahedrons, augmented truncated cubes, biaugmented truncated cubes, augmented truncated dodecahedrons, parabiaugmented truncated dodecahedrons, metabiaugmented truncated dodecahedrons, triaugmented truncated dodecahedrons, gyrate rhombicosidodecahedrons, parabigyrate rhombicosidodecahedrons, metabigyrate rhombicosidodecahedrons, trigyrate rhombicosidodecahedrons, diminished rhombicosidodecahedrons, paragyrate diminished rhombicosidodecahedrons, metagyrate diminished rhombicosidodecahedrons, bigyrate diminished rhombicosidodecahedrons, parabidiminished rhombicosidodecahedrons, metabidiminished rhombicosidodecahedrons, gyrate bidiminished rhombicosidodecahedrons, and tridiminished rhombicosidodecahedrons are envisaged. Snub disphenoids (Siamese dodecahedrons), snub square antiprisms, sphenocorona, augmented sphenocorona, sphenomegacorona, hebesphenomegacorona, disphenocingulum, bilunabirotunda, and triangular hebesphenorotunda and other miscellaneous non-uniform convex polyhedron shapes are contemplated.

In some embodiments, the average cross section of the cell fenestrations of the present invention is in the range of 0.01 to 2000 microns. More preferably, the average cross section of the cell fenestrations is in the range of 50 to 1000 microns. Most preferably, the average cross section of the cell fenestrations is in the range of 100 to 500 microns. Cell fenestrations can include, but are not limited to, (1) any openings created by the struts such as the open modified pores, e.g., 3804*a* of FIG. 38 or 1104 of FIGS. 11A-11F, created by the junctions, e.g., 3806 of FIG. 38 or nodes 1102 of FIGS. 11A-11F, or (2) any openings inscribed by the struts themselves, e.g., 2910 of FIG. 29B. For example, in embodiments where the cell fenestrations are generally circular, the average cross section of a fenestration may be the average diameter of that particular fenestration, and in embodiment where the cell fenestrations are generally rectangular or square, the average cross section of a fenestration may be the average distance going from one side to the opposite side.

Applying the above principles to other embodiments. FIGS. 51A and 51B illustrate a cell 5100 formed from an octahedron frame shown in FIG. 48 modified according to one embodiment of the present invention, shown in FIGS. 49-50. In FIG. 49, frame 4900 is formed by inscribing circles within the faces of frame 4800 in FIG. 48. In FIG. 50, frame 5000 is formed by removing frame 4800 from frame 4900 of FIG. 49. As shown in FIG. 49, the frame 5000 generally fits within the octahedron frame 4800. FIGS. 51A and 51B illustrate the completed cell 5100, which is formed by selecting a shape and thickness for frame 5000 in FIG. 50. Referring to FIGS. 51A and 51B, cell 5100 generally comprises eight curved struts 5102 that may be provided in the form of rings. The eight curved struts 5102 are connected to one another at twelve different junctions 5106. Six porous modified nodes 5104, each modified node having a generally rectangular shape are formed by the four different junctions 5106 and the corresponding struts 5102. As shown by FIGS. 51A and 51B, unlike the curved struts of cell 2500 of FIGS. 25A and 25B, curved struts 5102 have a rectangular or square cross-section rather than a circular cross-section of cells similar to cells 2500 in FIGS. 25A and 25B. Cells with a rectangular or square cross-section provide the porous structure with a roughness different than that of the cells with a circular cross-section. It is envisioned that struts of other embodiments can have different shapes for a cross-section. Accordingly, the struts of a cell can have the same cross-section, the shape of the cross-section of the struts can be randomly chosen, or the cross-section shape can be selectively picked to achieve the strength, porosity, and/or roughness desired.

As another alternative, FIGS. 53A-53D illustrate yet another cell 5300 based on a truncated tetrahedron frame shown in FIG. 52 as modified by one embodiment of the present invention. Referring to FIGS. 53A-53D, the cell 5300 is formed in a similar manner to cell 5100 of FIGS. 51A and 51B. That is, frame 5200 is inscribed with circles to form a second frame comprising circular struts, and frame 5200 is removed leaving behind the circular frame. Cell 5300 is completed by selecting a thickness and shape of the cross-sectional area for the frame 5300. As discussed above, the thickness and shape of the cross-section of the struts can be uniform or it can vary randomly or in a predetermined manner, including struts with a uniform cross-section or struts that are fluted. Cell 5300 includes four larger curved struts 5302*a* that correspond with the four large hexagonal sides of the truncated tetrahedral frame 5200 and four smaller curved struts 5202*b* that correspond with the four smaller triangular sides of the truncated tetrahedral frame 5200. Alternative, a cell can be formed by circumscribing a circle about the large sides 5202 and small sides 5204 of the truncated tetrahedral frame 5200. A 2-D representation of this alternative embodiment is shown in FIG. 36. While not expressly shown in the drawings, it is also contemplated that in some embodiments, combinations of inscribed and circumscribed curved struts may be employed. As illustrated in FIGS. 53A-53D, porous triangular modified nodes 5304 are formed between three junctions 5306 that connect the struts 5202*a* and 5202*b* together, but those skilled in the art will recognize that occluded modified nodes 3804*b* as shown in FIG. 38 may also be employed. Also, as shown in FIGS. 53A-53D, larger curved struts 5302*a* have a circular cross-section while smaller curved struts 5302*b* have a rectangular cross-section. FIGS. 54A-54E illustrate various angles of a porous structure formed by stacking cells 5300 of FIG. 53 in one exemplary manner. It is envisioned that that in some embodiments, cells 5300 of FIG. 53 can be stacked in different manners as known be a person skilled in the art.

Figure 56B:
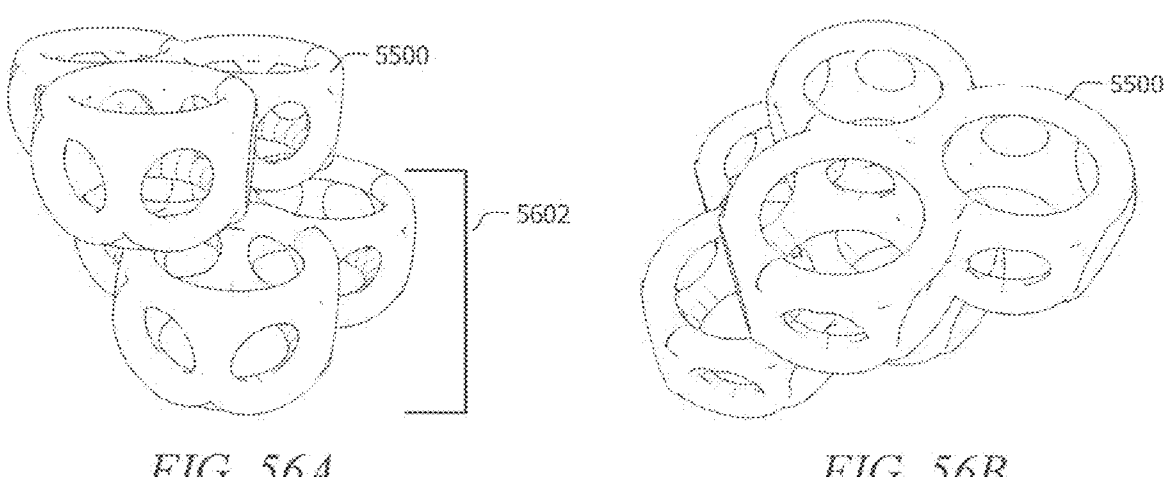
Figure 56B:
Figure 57A:
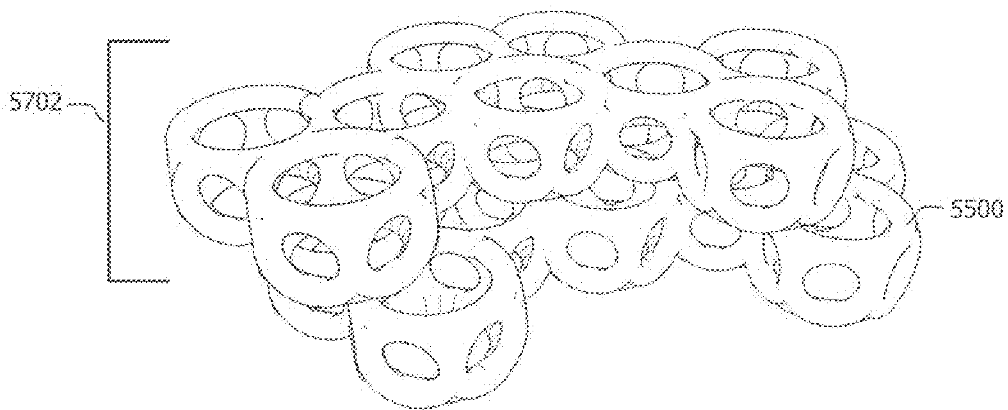
Figure 57B:
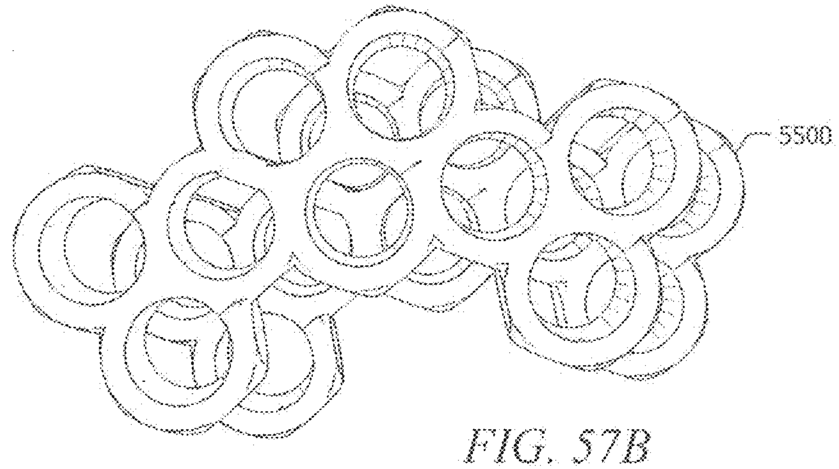
Figure 58:
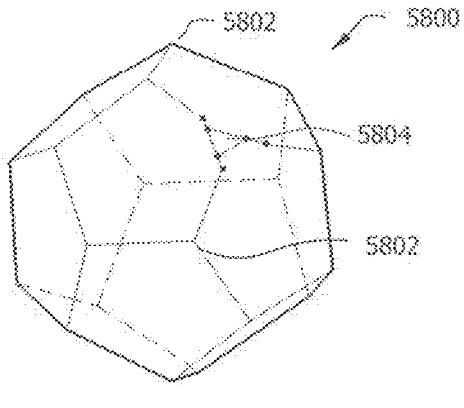
FIGS. 58-61 illustrate 3-D representations of frames based on a dodecahedron modified by various embodiments of the present invention.
Figure 59:
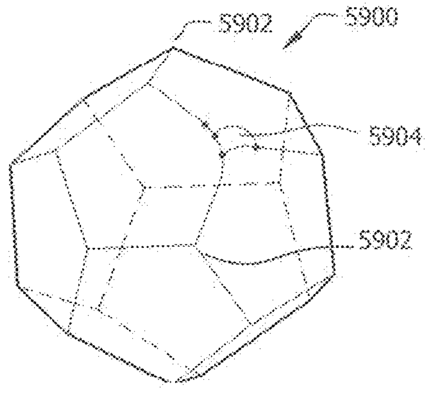
Figure 60:
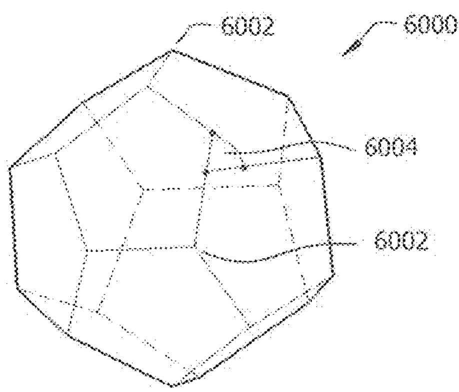
Figure 61:
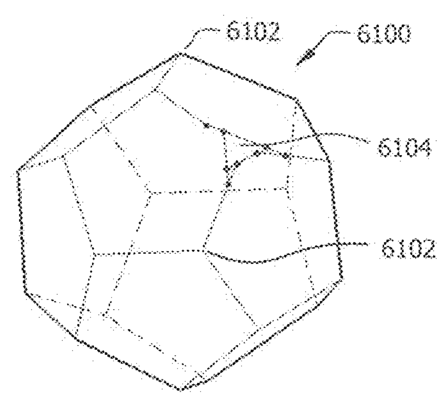

FIGS. 55A-55E illustrate yet another embodiment where a cell 5500 is based on a hexagonal prism (Prismatic) frame with upper and lower hexagons and that includes six vertical sides. The six smaller curved struts 5502*a* are used for the six sides and larger upper and lower curved struts 5502*b* are used for the top and bottom. In the cell 5500 illustrated in FIGS. 55A-55E, the eight curved struts 5302*a*, 5302*b* are connected by occluded modified nodes 5504 but, it will be apparent to those skilled in the art that porous modified nodes such as those shown in FIG. 25 may also be employed. In the particular embodiment shown in FIGS. 55A-55E, the six smaller curved struts 5502*a* used for the six sides have a slightly smaller cross-sectional area than the two larger upper and lower curved struts 5302*b*. However, it would be apparent to those skilled in the art that the struts with uniform or substantially uniform cross-sectional areas can also be employed without departing from the scope of this disclosure. FIGS. 56A-56B illustrate various angles of a porous structure formed by stacking cells 5500 of FIGS. 55A-55E in one exemplary manner. In FIGS. 56A and 56B, cells 5500 are placed adjacent to one another to form a layer 5602 and the layers are placed on top of one another either in a predetermined or random manner. FIGS. 57A and 57B similarly show a greater number of cells 5500 stacked in the same manner as shown in FIGS. 56A and 56B. As seen, cells 5500 are stacked by layers 5702. It is envisioned that in some embodiment, cells 5500 of FIG. 55 can be stacked in different manners as known to a person skilled in the art.

FIGS. 58-61 illustrate dodecahedral frames 5800, 5900, 6000, and 6100 modified according to another embodiment of the invention. Instead of using curved struts or struts with curved portions to eliminate or reduce conventional nodes 5802, 5902, 6002, and 6102, the particular embodiments of FIGS. 58-61 adjust the conventional nodes by ensuring at least one of the conventional nodes have no more than two node intersecting at a node as shown by at least FIGS. 11A-11F. As shown by FIGS. 58-61, frames 5800, 5900, 6000, and 6100 have at least one modified node 5804, 5904, 6004, and 6104.

In some embodiment, the configurations of the cells, struts, nodes and/or junctions may vary randomly throughout the porous structure to more closely simulate natural bone tissue. Particularly, the cells formed according to the present invention, such as the cells illustrated in FIG. 25A-25B, 29A, 37A-37B, 38, 39A-39C, 42, 51A-51B, 53A-53D, or 35A-55B, can be stacked or repeated according to the methods outlined in U.S. Application No. 61/260,811, the disclosure of which am incorporated by reference herein in its entirety. In addition, the methods of U.S. Application No. 61/260,811 can also be employed to modify conventional nodes such that no more than two struts intersect at a node. In yet another embodiment, the porous structure formed according to the invention can be used in medical implants, such as an orthopedic implant, dental implant, or vascular implant.

As further discussed in the following paragraphs, the present disclosure also provides for a method to fabricate the porous structures described above. Preferably, the improved porous structures of the present invention is formed by using a free-form fabrication method, including rapid manufacturing techniques (RMT) such as direct metal fabrication (DMF). Generally, in free-form fabrication techniques, the desired structures can be formed directly from computer controlled databases, which greatly reduces the time and expense required to fabricate various articles and structures. Typically in RMT or free-form fabrication employs a computer-aided machine or apparatus that has an energy source such as a laser beam to melt or sinter powder to build the structure one layer at a time according to the model selected in the database of the computer component of the machine.

For example, RMT is an additive fabrication technique for manufacturing objects by sequential delivering energy and/or material to specified points in space to produce that part. Particularly, the objects can be produced in a layer-wise fashion from laser-fusible powders that are dispensed one layer at a time. The powder is fused, melted, remelted, or sintered, by application of the laser energy that is directed in raster-scan fashion to portions of the powder layer corresponding to a cross section of the object. After fusing the powder on one particular layer, an additional layer of powder is dispensed, and the process is repeated until the object is completed.

Detailed descriptions of selective laser sintering technology may be found in U.S. Pat. Nos. 4,863,538; 5,017,753; 5,076,869; and 4,944,817, the disclosures of which are incorporated by reference herein in their entirety. Current practice is to control the manufacturing process by computer using a mathematical model created with the aid of a computer. Consequently, RMT such as selective laser remelting and sintering technologies have enabled the direct manufacture of solid or 3-D structures of high resolution and dimensional accuracy from a variety of materials.

In one embodiment of the present invention, the porous structure is formed from powder that is selected from the group consisting of metal, ceramic, metal-ceramic (cermet), glass, glass-ceramic, polymer, composite, and combinations thereof. In another embodiment, metallic powder is used and is selected from the group consisting of titanium, titanium alloy, zirconium, zirconium alloy, niobium, niobium alloy, tantalum, tantalum alloy, nickel-chromium, (e.g., stainless steel), cobalt-chromium alloy and combinations thereof.

As known by those skilled in the art, creating models of cells or structures according to the disclosure of the present invention can be done with computer aided design (CAD) software or other similar software. In one embodiment, the model is built by starting with a prior art configuration and modifying the struts and nodes of the prior art configuration by either (1) adjusting the number struts that intersect at a node, such as the configurations in FIGS. 3-8, 11A-11F, 12A-12D, 17-20, or 22-23, or (2) introduce curved portions to the struts such as the configurations in FIG. 13A-13M, 14, 15A-15C, 16, or 58-61. In another embodiment, curved "ring-like" struts can be added to form cell illustrated in FIG. 25A-25B, 29A, 37A-37B, 38, 39A-39C, 42, 51A-51B, 53A-53D, or 55A-55B. Referring to FIG. 26, in one embodiment, these cells can be formed by starting with a frame 2600 based on a polyhedron, such as a dodecahedron. Referring to FIG. 27, the next step is to inscribe circles within each face of the frame 2600 to form frame 2700, which is frame 2800 superimposed on frame 2600. Subsequently, frame 2600 can be removed from frame 2700, leaving only frame 2800. The thickness and shape of the cross-section of frame 2800 can be selected to form a completed cell, such as cell 2900 in FIG. 29A. As discussed above, a portion of the faces of frame 2600 can be inscribed with circles and/or a portion of frame 2600 can be removed to form, or frame 2600 is not removed at all. The cells formed by such combinations are illustrated in FIGS. 37A-37B, 38, and 39A-39C. As shown by FIGS. 48-53 and 55, the same steps can be applied to any type of frames based on a polyhedron. Also with the aid of computer software, stacking, tiling, or repeating algorithm can be applied to create a model of a porous structure with the desired dimensions formed from unit cells or struts and nodes of the present invention. One such stacking algorithm is space filling tessellation shown by FIGS. 43-45. As mentioned above, the methods disclosed in U.S. Application No. 61/260,811, which is incorporated by reference herein in its entirety, can be applied to stack the cells of the present invention or to form the struts according to the disclosures of the present invention by controlled randomization.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A porous structure comprising:
- a plurality of struts, each strut comprising an elongated body portion between a first end and a second end; and
- a plurality of nodes, wherein each node comprises an intersection of at least an end of a first strut, an end of a second strut, and an end of a third strut;
- wherein at least three of the struts intersect at each of the plurality of nodes;
- wherein at least some struts of the plurality of struts have a different length from at least some other struts of the plurality of struts; and
- wherein some of the struts are straight and some of the struts are curved.

2. The structure of claim 1, wherein a cross-sectional shape of each of the plurality of struts varies randomly.

3. The structure of claim 1, wherein a first end of at least one strut has a first random diameter, a second end of the at least one strut has a second random diameter, and the elongated body portion of the at least one strut has a third random diameter, wherein the first and second diameters are larger than the third diameter.

4. The structure of claim 3, wherein:

the first end of the at least one strut is a fluted end portion that flares from the third diameter to the first diameter; and the second end of the at least one strut is a fluted end portion that flares from the third diameter to the second diameter.

5. The structure of claim 4, wherein the first and second end portions flare in a parabolic fluted shape or a tapered frusto-conic shape.

6. The structure of claim 1, wherein some or all of the struts randomly grow or shrink in cross-sectional circumference along a predetermined length of the body portion of the strut.

7. The structure of claim 1, wherein a length of the elongated body portion of each strut varies randomly.

8. The structure of claim 1, wherein:

the structure forms a multi-sided cell in a larger structure; and an overall size, shape, and number of sides of at least some of the cells varies.

9. The structure of claim 1, wherein the structure forms a polyhedral cell.

10. The structure of claim 9, wherein the polyhedral cell is a structure having between 4 and 24 sides.

11. The structure of claim 1, further comprising a plurality of open pores defined between the struts.

12. The structure of claim 11, wherein the plurality of open pores are asymmetrical in shape.

13. The structure of claim 1, wherein the structure is formed by a rapid manufacturing technique.

14. The structure of claim 13, wherein the structure is formed from a material selected from a group consisting of metal, ceramic, metal-ceramic (cermet), glass, glass-ceramic, polymer, composite, and combinations thereof.

15. The structure of claim 13, wherein the structure is formed from a metallic powder selected from a group consisting of titanium, titanium alloy, zirconium, zirconium alloy, niobium, niobium alloy, tantalum, tantalum alloy, nickel-chromium, cobalt-chromium alloy, and combinations thereof.

16. The structure of claim 1, wherein the structure is biocompatible.

17. A porous structure comprising:

a plurality of struts, each strut comprising an elongated body portion between a first end and a second end;

a plurality of nodes, wherein each node comprises an intersection of at least an end of a first strut, an end of a second strut, and an end of a third strut; and a plurality of open pores defined between the plurality of struts;

wherein at least three of the struts intersect at each of the plurality of nodes; and wherein at least some struts of the plurality of struts have a different length from at least some other struts of the plurality of struts.

18. The structure of claim 17, wherein some of the struts are straight and some of the struts are curved.

19. The structure of claim 17, wherein a cross-sectional shape of each of the plurality of struts varies randomly.

20. The structure of claim 17, wherein a first end of at least one strut has a first random diameter, a second end of the at least one strut has a second random diameter, and the elongated body portion of the at least one strut has a third random diameter, wherein the first and second diameters are larger than the third diameter.

21. The structure of claim 20, wherein:

the first end of the at least one strut is a fluted end portion that flares from the third diameter to the first diameter; and the second end of the at least one strut is a fluted end portion that flares from the third diameter to the second diameter.

22. The structure of claim 21, wherein the first and second end portions flare in a parabolic fluted shape or a tapered frusto-conic shape.

23. The structure of claim 17, wherein some or all of the struts randomly grow or shrink in cross-sectional circumference along a predetermined length of the body portion of the strut.

24. The structure of claim 17, wherein a length of the elongated body portion of each strut varies randomly.

25. The structure of claim 17, wherein:

the structure forms a multi-sided cell in a larger structure; and an overall size, shape, and number of sides of at least some of the cells varies.

26. The structure of claim 17, wherein the structure forms a polyhedral cell.

27. The structure of claim 26, wherein the polyhedral cell is a structure having between 4 and 24 sides.

28. The structure of claim 17, wherein the plurality of open pores are asymmetrical in shape.

29. The structure of claim 17, wherein the structure is formed by a rapid manufacturing technique.

30. The structure of claim 29, wherein the structure is formed from a material selected from a group consisting of metal, ceramic, metal-ceramic (cermet), glass, glass-ceramic, polymer, composite, and combinations thereof.

31. The structure of claim 29, wherein the structure is formed from a metallic powder selected from a group consisting of titanium, titanium alloy, zirconium, zirconium alloy, niobium, niobium alloy, tantalum, tantalum alloy, nickel-chromium, cobalt-chromium alloy, and combinations thereof.

32. The structure of claim 17, wherein the structure is biocompatible.

33. A porous structure comprising:

a plurality of struts, each strut comprising an elongated body portion between a first end and a second end;

a plurality of nodes, wherein each node comprises an intersection of at least an end of a first strut, an end of a second strut, and an end of a third strut; and wherein at least three of the struts intersect at each of the plurality of nodes;

wherein at least some struts of the plurality of struts have a different length from at least some other struts of the plurality of struts; and wherein a cross-sectional shape of each of the plurality of struts varies randomly.

34. A porous structure comprising:

a plurality of struts, each strut comprising an elongated body portion between a first end and a second end;

a plurality of nodes, wherein each node comprises an intersection of at least an end of a first strut, an end of a second strut, and an end of a third strut; and wherein at least three of the struts intersect at each of the plurality of nodes;

wherein at least some struts of the plurality of struts have a different length from at least some other struts of the plurality of struts; and wherein a first end of at least one strut has a first random diameter, a second end of the at least one strut has a second random diameter, and the elongated body portion of the at least one strut has a third random diameter, wherein the first and second diameters are larger than the third diameter.

35. A porous structure comprising:

a plurality of struts, each strut comprising an elongated body portion between a first end and a second end;

a plurality of nodes, wherein each node comprises an intersection of at least an end of a first strut, an end of a second strut, and an end of a third strut; and wherein at least three of the struts intersect at each of the plurality of nodes;

wherein at least some struts of the plurality of struts have a different length from at least some other struts of the plurality of struts; and wherein some or all of the struts randomly grow or shrink in cross-sectional circumference along a predetermined length of the body portion of the strut.

36. A porous structure comprising:

a plurality of struts, each strut comprising an elongated body portion between a first end and a second end;

a plurality of nodes, wherein each node comprises an intersection of at least an end of a first strut, an end of a second strut, and an end of a third strut; and wherein at least three of the struts intersect at each of the plurality of nodes;

wherein at least some struts of the plurality of struts have a different length from at least some other struts of the plurality of struts; and wherein a length of the elongated body portion of each strut varies randomly.

* * * * *